U S009687175B2

(12) United States Patent
Forsell

(10) Patent No.: US 9,687,175 B2
(45) Date of Patent: *Jun. 27, 2017

(54) VOICE CONTROL SYSTEM FOR AN IMPLANT

(71) Applicant: Peter Forsell, Bouveret (CH)

(72) Inventor: Peter Forsell, Bouveret (CH)

(*) Notice: Subject to any disclaimer, the term of this patent is extended or adjusted under 35 U.S.C. 154(b) by 4 days.

This patent is subject to a terminal disclaimer.

(21) Appl. No.: 14/455,915

(22) Filed: Aug. 10, 2014

(65) Prior Publication Data
US 2015/0120298 A1 Apr. 30, 2015

Related U.S. Application Data

(63) Continuation of application No. 13/384,382, filed as application No. PCT/SE2010/050854 on Jul. 19, 2010, now Pat. No. 8,838,458.

(Continued)

(30) Foreign Application Priority Data

Jul. 17, 2009 (SE) ...................................... 0901000

(51) Int. Cl.
| | | |
|---|---|---|
| *G10L 15/00* | (2013.01) | |
| *A61B 5/07* | (2006.01) | |
| *A61N 1/372* | (2006.01) | |
| *A61N 1/378* | (2006.01) | |
| *H04B 13/00* | (2006.01) | |
| *G10L 15/06* | (2013.01) | |
| *A61B 5/00* | (2006.01) | |

(52) U.S. Cl.
CPC ............ *A61B 5/076* (2013.01); *A61B 5/0028* (2013.01); *A61B 5/0031* (2013.01); *A61B 5/749* (2013.01); *A61N 1/3727* (2013.01); *A61N 1/3787* (2013.01); *A61N 1/37217* (2013.01); *G10L 15/00* (2013.01); *G10L 15/063* (2013.01); *H04B 13/005* (2013.01); *A61B 5/0082* (2013.01); *A61B 5/7239* (2013.01)

(58) Field of Classification Search
CPC ..... A61B 5/0002; A61B 5/0028; G10L 15/00; H04B 13/005
USPC .......................................... 704/275
See application file for complete search history.

(56) References Cited

U.S. PATENT DOCUMENTS

| | | | | |
|---|---|---|---|---|
| 4,731,811 | A * | 3/1988 | Dubus ................... | H04M 1/271 379/355.09 |
| 5,040,212 | A * | 8/1991 | Bethards ................. | G10L 15/00 704/246 |
| 5,117,460 | A * | 5/1992 | Berry ...................... | G10L 15/00 340/7.39 |

FOREIGN PATENT DOCUMENTS

WO 2009056167 A1 5/2009

\* cited by examiner

*Primary Examiner* — Daniel Abebe
(74) *Attorney, Agent, or Firm* — Gabriela B. Tomescu; Bergenstrahle & Partners AB

(57) ABSTRACT

A system for the control of an implant (32) in a body (11), comprising first (10, 20) and second parts (12) which communicate with each other. The first part (10, 20) is adapted for implantation and for control of and communication with the medical implant (32), and the second part (12) is adapted to be worn on the outside of the body (11) in contact with the body and to receive control commands from a user and to transmit them to the first part (10, 20). The body (11) is used as a conductor for communication between the first (10, 20) and the second (12) parts. The second part (12) is adapted to receive and recognize voice control (Continued)

commands from a user and to transform them into signals which are transmitted to the first part (10, 20) via the body (11).

20 Claims, 13 Drawing Sheets

Related U.S. Application Data

(60) Provisional application No. 61/213,807, filed on Jul. 17, 2009.

VOICE CONTROL SYSTEM FOR AN IMPLANT

This application is a continuation of U.S. application Ser. No. 13/384,382, filed Jan. 17, 2012, which is the U.S. National phase of International Application No. PCT/SE2010/050854, filed 19 Jul. 2010, which designated the U.S. and claims the benefit of U.S. Provisional Application No. 61/213,807, filed 17 Jul. 2009, and Swedish Application 0901000-0, filed 17 Jul. 2009, the entire contents of each of which are hereby Incorporated by reference.

TECHNICAL FIELD

The present invention discloses a control system for an implant in a mammal body, by means of which the implant can be controlled using voice commands.

BACKGROUND

Medical implants as such are previously known, and are often used to replace or assist an organ or a function in a mammal body. Some medical implants which may be mentioned by way of example are artificial hip joints, pacemakers, artificial insulin pumps and the like.

As will be understood, some implants require, or may be improved by, the ability to receive input from a user of the implant, either from the patient or medical personnel attending to the patient. Various methods are known for giving such input to implanted devices. For example, U.S. Pat. No. 5,569,186 to Snell et al discloses a glucose pump system, parts of which are implantable in a human body, where the operation of the system may be monitored and controlled from a monitor external to the human body, with the monitor being a wrist-worn device. The monitor of the Snell patent can display information from and send commands to the rest of the system by means of telemetry signals, i.e. radio control.

SUMMARY

It is an object of the present invention to improve the comfort, ease and reliability with which a medical implant in a mammal body such as a human body may be controlled.

This object is achieved by the present invention in that it discloses a system for the control of a medical implant in a mammal body. The system of the invention comprises a first and a second part which are adapted for communication with each other; the first part is adapted for implantation in the mammal body for the control of and communication with the medical implant, and the second part is adapted to be worn on the outside of the mammal body in physical contact with said body.

In addition, the second part is adapted to receive control commands from a user and to transmit these commands to the first part, and the system of the invention is adapted to use the mammal body as a conductor for communication between the first and the second parts.

Furthermore, the second part of the system is adapted to receive and recognize control commands from a user as voice commands and is also adapted to transform recognized voice commands into signals which are then transmitted to the first part via the mammal body as a conductor for the control of said implant.

Thus, by means of the system of the invention, the user of an implant, or medical personnel or others who help the user, can control the implant by means of spoken commands. In addition, the need for radio transmitters etc as exhibited by other systems in the field of implant control is obviated by means of the present invention, since the system of the invention uses the body of the user as a conductor for the communication between the first and second parts of the implant.

The body is used as a conductor for communication by means of creating an electrical (capacitive) field between the first and second parts of the system, which field may then be used for communicating between the two parts, by altering the field.

An alternative embodiment involves a system for the control of a medical implant (32) in a mammal body (11), said system comprising a first (10, 20) and a second part (12) being adapted for communication with each other, in which system the first part (10, 20) is adapted for implantation in the mammal body (11) for the control of and communication with the medical implant (32), the second part (12) is adapted to be worn on the outside of the mammal body (11) in physical contact with said body and adapted to receive control commands from a user and to transmit these commands to the first part (10, 20), characterized in that the system is adapted to use the mammal body (11) as a conductor for communication between the first (10, 20) and the second (12) parts and in that the second part (12) is adapted to receive and recognize the control commands from a user as voice commands and is adapted to transform recognized voice commands into signals which are transmitted to the first part (10, 20) via the mammal body (11) as a conductor for the control of said implant (32), the first part (10, 20) being adapted to convey such signals to the implant (32), wherein said second part (12) comprises a learning device adapted to successively learn the voice commands and learn to combine with the right output command.

Yet another embodiment includes a system for the control of a medical implant (32) in a mammal body (11), said system comprising a first (10, 20) and a second part (12) being adapted for communication with each other, in which system the first part (10, 20) is adapted for implantation in the mammal body (11) for the control of and communication with the medical implant (32), the second part (12) is adapted to be worn on the outside of the mammal body (11) in physical contact with said body and adapted to receive control commands from a user and to transmit these commands to the first part (10, 20), characterized in that the system is adapted to use the mammal body (11) as a conductor for communication between the first (10, 20) and the second (12) parts and in that the second part (12) is adapted to receive and recognize the control commands from a user as voice commands and is adapted to transform recognized voice commands into signals which are transmitted to the first part (10, 20) via the mammal body (11) as a conductor for the control of said implant (32), the first part (10, 20) being adapted to convey such signals to the implant (32), wherein said voice commands comprise a complex of different frequencies translated into one fixed defined output command, wherein said system comprising a first conducting plate (29) in the first part (10, 20) of the system and a second conducting plate (27) in the second part (12) of the system, the system being adapted to create an electrical capacitive field with potential differences between said first (29) and second (27) conducting plates.

The system may further comprise a detector circuit (30) in the first part (10, 20) of the system for detecting the potential differences between the conducting plates (27, 29), the system being adapted to use the potential differences for said communication between the first (10, 20) and the second (12) parts of the system.

In an alternative embodiment of the system the second part (12) comprises a learning device adapted to successively learn the voice commands and learn to combine with the right output command.

Preferable said learning device of the second part (12) is adapted to recognise approximate voice commands into a fixed defined output command.

In yet another embodiment said voice commands comprise a complex of different frequencies translated into one fixed defined output command.

Preferably said output commands do not differentiate different frequencies, but instead summarise a defined input of different frequencies into one single action.

BRIEF DESCRIPTION OF THE DRAWINGS

The invention will be described in more detail in the following, with reference to the appended drawings, in which.

DETAILED DESCRIPTION

Figure 1:
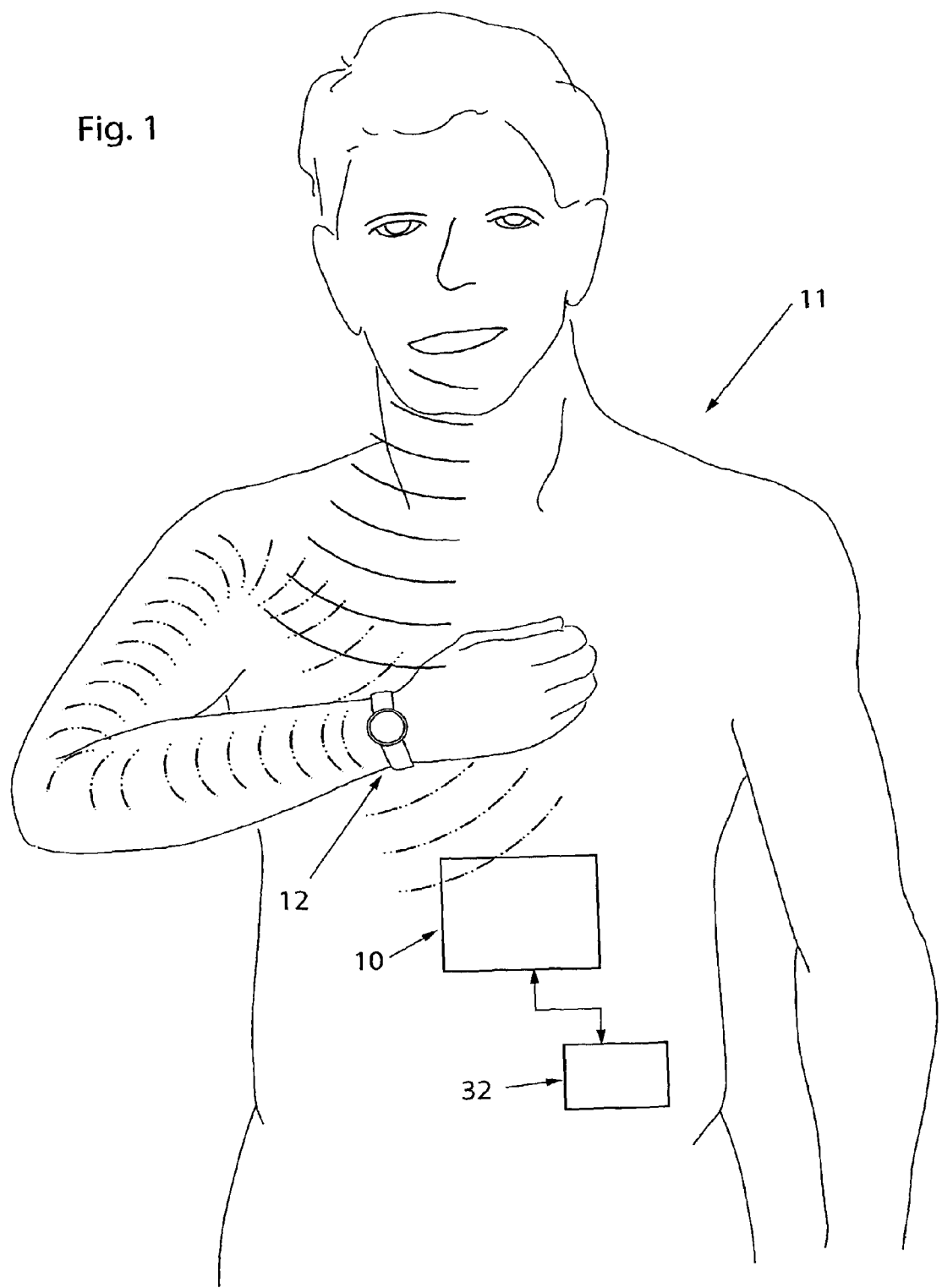
FIG. 1 shows an overview of the system of the invention.

FIG. 1 shows an overview intended to illustrate the system of the invention, and its use and application. As has been mentioned above, the inventive system is intended for use with a medical implant in a mammal body, such as the human body, and FIG. 1 shows a human user 11 who has been equipped with an implant 32. The implant 32 is shown in FIG. 1 as being located in the abdominal region of the user, but this is merely an example intended to illustrate a generic implant with which the invention can be used; such an implant can be located in more or less any region of the mammal body, depending on the nature and function of the implant.

The implant 32 can be of various kinds, all of which are within the scope of the present invention, but examples of which mention may be made include the following:

A controllable engine,
A pump,
A stimulation device,
A constriction device,
A fluid moving device,
A heart pump,
A heart valve,
A filtering device,
A pharmaceutical drug delivery device,
An artificial reservoir,
A fertility or non-fertility device,
A no-reflux device,
A potency treatment device,
A urine incontinence or urine retention device,
An intestinal device,
An aneurysm treatment device,
A hypertension treatment device,
A clot removing device The system of the invention is adapted to control the implant 32, and to this end the system comprises a first part 10 which is adapted for implantation in the mammal body, and a second part 12 which is adapted to be worn on the outside of the mammal body in physical contact with the body.

As indicated in FIG. 1, the second part 12 is adapted to receive and recognize control commands from a user in the form of voice commands (i.e. spoken commands), and to transform recognized voice commands into signals which are transmitted to the first part 10. In other words, the second part 12 is adapted to recognize a number of spoken commands, such as, for example, "more", "less", "on", "off", "open", "close", and to transform these spoken commands into signals in a form which can be transmitted to and understood by the first part 10 of the system, i.e. the part which is implanted in the body 11.

The first part 10 is adapted to, upon receiving such commands from the second 12 part of the system, convey them to the implant 32 for control of the implant.

According to the present invention, the second part 12 transmits the signals (i.e. the control commands) to the first part 10 via the mammal body 11 as a conductor, which is done by creating a capacitive field between the first 10 and the second 12 parts of the system, and then creating variations in that field in order to use those variations for the communication between the two parts of the system.

Below, various ways of creating the capacitive field will be described, and details will then be given on how the capacitive field and variations in it can be used by the present invention for communication between the two parts of the system. It should also be pointed out that the present invention makes use of the mammal body's conducting properties for the communication: the electrical field which is created will propagate throughout the body due to the body's conductivity, and can thus be created at one point in the body and detected at another point in the body. In a way, the body is thus used as an "antenna" or conductor by the present invention for the communication between the two parts of the system.

Figure 2:
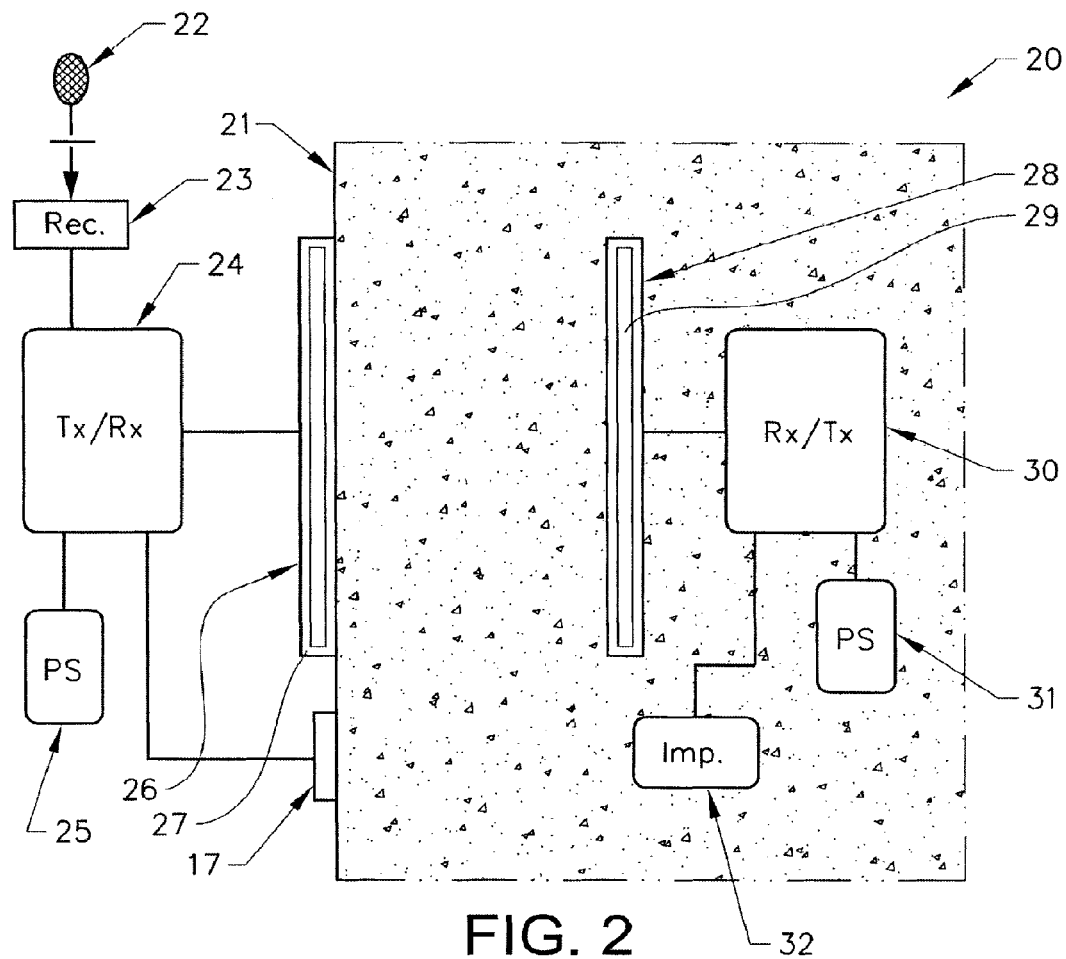
FIG. 2 shows a block diagram of a first embodiment.

An embodiment according to the combination of FIGS. 1 and 2, involves a system for the control of a medical implant (32) in a mammal body (11), said system comprising a first (10, 20) and a second part (12) being adapted for communication with each other, in which system the first part (10, 20) is adapted for implantation in the mammal body (11) for the control of and communication with the medical implant (32), the second part (12) is adapted to be worn on the outside of the mammal body (11) in physical contact with said body and adapted to receive control commands from a user and to transmit these commands to the first part (10, 20). The system is adapted to use the mammal body (11) as a conductor for communication between the first (10, 20) and the second (12) parts and in that the second part (12) is adapted to receive and recognize the control commands from a user as voice commands and is adapted to transform recognized voice commands into signals which are transmitted to the first part (10, 20) via the mammal body (11) as a conductor for the control of said implant (32), the first part (10, 20) being adapted to convey such signals to the implant (32), wherein said second part (12) comprise a learning device adapted to successively learn the voice commands and learn to combine with the right output command.

Yet another embodiment includes a system for the control of a medical implant (32) in a mammal body (11), said system comprising a first (10, 20) and a second part (12) being adapted for communication with each other, in which system the first part (10, 20) is adapted for implantation in the mammal body (11) for the control of and communication with the medical implant (32), the second part (12) is adapted to be worn on the outside of the mammal body (11) in physical contact with said body and adapted to receive control commands from a user and to transmit these commands to the first part (10, 20), characterized in that the system is adapted to use the mammal body (11) as a conductor for communication between the first (10, 20) and the second (12) parts and in that the second part (12) is adapted to receive and recognize the control commands from a user as voice commands and is adapted to transform recognized voice commands into signals which are transmitted to the first part (10, 20) via the mammal body (11) as a conductor for the control of said implant (32), the first part (10, 20) being adapted to convey such signals to the implant (32), wherein said voice commands comprise a complex of different frequencies translated into one fixed defined output command, wherein said system comprising a first conducting plate (29) in the first part (10, 20) of the system and a second conducting plate (27) in the second part (12) of the system, the system being adapted to create an electrical capacitive field with potential differences between said first (29) and second (27) conducting plates.

The system may further comprise a detector circuit (30) in the first part (10, 20) of the system for detecting the potential differences between the conducting plates (27, 29), the system being adapted to use the potential differences for said communication between the first (10, 20) and the second (12) parts of the system.

In an alternative embodiment of the system the second part (12) comprises a learning device adapted to successively learn the voice commands and learn to combine with the right output command.

Preferably the learning device of the second part (12) is adapted to recognise approximate voice commands into a fixed defined output command.

In yet another embodiment said voice commands comprise a complex of different frequencies translated into one fixed defined output command.

Preferably said output commands do not differentiate different frequencies, but instead summarise a defined input of different frequencies into one single action.

FIG. 2 shows a block diagram of one embodiment of a system 20 of the invention: a part of a mammal body is shown, with the skin indicted as a line 21. As shown in FIG. 2, the second part of the system 20, i.e. the part which is intended to be worn on the outside of the mammal's body, comprises a device, symbolically shown as microphone 22, for detecting spoken commands from a user of the system, i.e. either the patient or e.g. medical personnel attending to the patient, which spoken commands are intended to control a device 32 which has been implanted in the patient.

In addition, the second part of the system 20 comprises a device 23 for recognizing spoken commands, and for "translating" them into signals or commands which can be understood by the implant 32. The signals or commands which can be recognized by the implant 32 can vary depending on how the implant 32 is designed, but can for example be commands in the form of ASCII characters, binary numbers etc.

For example, in order to illustrate this principle, assume a command which indicates that the implant 32 should increase an activity which it can perform. Assume further that the input to the implant 32 which causes the implant to increase this activity is "binary four", i.e. 1 0 0; the recognition device 23 will then, when it recognizes the spoken command "increase", have as its output "binary four", i.e. 1 0 0, which can then be transmitted to the implant 32 in a manner which will be described below.

The recognition device 23 can in one embodiment be such that it is a learning device with a set number of output commands, or it can, if the technology permits, be such that it "understands" voice commands without any learning procedure. In either case, i.e. learning or non-learning, the recognition device is suitably "taught" by a user which spoken command that should be matched to one of a set of commands which the implant 32 can accept as input.

In the case of a learning device, then, in the example given above, with the spoken command "increase", the recognition device 23 will be exposed to this word from an authorized user a number of times; the recognition device 23 indicates to the user that the word has been "learnt", i.e. that the recognition device can recognize that particular word or phrase from that particular speaker in the future; the authorized user will then match this word or phrase to the output "binary four". The notion of "authorized user" is intended to prevent the system 20 of the invention from outputting commands to the medical implant 32 when they are spoken by non-authorized personnel. Naturally, a recognition device which can recognize the same word or phrase from a set of authorized users can also be used within the scope of the present invention.

As is also shown in FIG. 2, the second part of the system 20 comprises a send/receive circuit 24 for generating the actual commands to the implant 32. The second part also comprises a second capacitor plate 27 which is connected (suitably by wire, as shown in FIG. 2) to the send/receive device 24. As shown in FIG. 2, the first part of the system also comprises a first capacitor plate 29, which is implanted in the patient since it is comprised in the first part of the system.

The second part of the system may also comprise a grounding plate 17, which is in close or direct contact with the mammal body 11.

According to the invention, the system 20 is adapted to create a capacitive field between the first and the second capacitive plates 29, 27, and to create variations in this field by means of which commands can be transmitted to the first part from the second part, and from there to the implanted device 32, which is connected to the first part of the system, suitably by wire, as indicated in FIG. 2, although wireless solutions are also within the scope of the invention.

A fact which is used by the present invention is that a mammal body will act as a conductor for a capacitive field, so that "signals" i.e. variations in the capacitive field will propagate between the two parts of the system by means of the body as a conductor.

Suitably, as shown in FIG. 2, one or both of the capacitive plates 27, 29 are covered in a dielectric material 26, 28.

The second part of the system 20 also comprises a power supply 25, which is shown in FIG. 2. Suitably but not necessarily this power supply 25 is a battery or some other form of portable power supply. The first part also comprises a power supply, shown as 31 in FIG. 2. The power supply 31 will be commented on in more depth later in this text.

Turning now to the first part of the system 20, i.e. the part which is intended to be implanted in the mammal patient and to be connected to the medical implant 32 in order to transmit commands to it, and possibly also to receive signals from the implant 32 which are to be communicated to the user of the implant, the first part comprises, as shown in FIG. 2, the following major components: the capacitor plate 29, as described above, with a possible dielectric cover 28, and a receive (and possibly transmit) device 30 connected to the capacitor plate 29 in order to detect the capacitive field and variations in it.

The first part also comprises a power supply 31, which will be described in more detail below.

Turning now to more specific details of how a capacitive field can be created by a system of the invention, and used by the system for communication between the first and second parts of the system, the following can be said:

As has been pointed out previously in this text, the inventive system uses the realization that by using the patient's body as a communication medium or conductor, and by creating and detecting (measuring) variations in a capacitive field, i.e. measuring the electric potential in different places, communication between a first implanted part of the system and a second external (to the body) part, communication can be established with a minimum of electric current flowing through the body, and the communication can be used by the first implanted part for controlling and communicating with a medical implant.

Thus, for the communication of the invention, at least a portion of the patient's body is used as a conductor. Generally, the internal communication unit, i.e. the first part of the system 20 comprises a communication receiver, and for a transmitter or a transceiver 30 that includes one part of a capacitive energy storage. The communicating of information using the capacitive coupling includes letting an electrical current be injected into or drawn from the capacitive energy storage: In the system, the information can e.g. be represented as variations of the derivative of the voltage over the capacitive energy storage, i.e. as transitions in the voltage level.

The information may be coded according to the Manchester system, and dual frequency communication can be used.

With renewed reference to FIG. 2 and the system 20 shown there, as is shown at least one of the capacitor plates 27, 29, is embedded in an electrical insulator, i.e. a dielectric material 26, 28, which suitably forms a thin layer which totally surrounds the respective plate, the plates being made from an electrically conducting material, e.g. copper. The electrical resistance between the capacitor plates should be as high as possible, e.g. at least 1 MΩ.

The capacitor plates 27, 29 are electrically coupled to the transmit and/or receive circuits 24, 30, which can also be seen as "driver circuits", which basically can include transmitter and/or receiver circuits, or, where applicable, transceiver circuits. The driver circuits 30 for the internal capacitor plate 29 are thus also adapted for implantation and for electrical connection to the implanted device or a control device therefore, shown as 32. The external driver circuits 24 are connected to a control device, which is not shown in FIG. 2.

The driver circuits 24, 30 are powered by power supplies 25, 31, with the internal power supply 31 also being adapted for implantation. The driver circuits may require a common electrical ground potential which can make the transfer of information more secure, which can be provided by e.g. having the housing of the internal driver circuits 30 be electrically conducting, and thus in electrical contact with the body tissues. The external driver circuits 24 can be electrically connected to an electrically conducting plate or electrode 17 that is electrically attached to the skin of the person's body in the same way as electrodes for e.g. cardiography.

The capacitor formed by the capacitor plates 27, 29 is part of an electric circuit connection between the driver circuits 24, 30, and electrical signals can be transmitted over this circuit connection. By selecting the dimensions of the plates and their location in relation to each other, the capacitor which is thus formed can be given a capacitance suited for the signal transfer. Hence, the plates 27, 29 can be made to have as large a surface area as is possible for an implant, e.g. in the range of 2-8 $cm^2$, and can be configured in a suitable way. Of course, the plates may also be rectangular or in the shape of squares, but they may also e.g. have an elongated round shape or a circular shape. In particular, the internal capacitor plate 29 can be given a shape which makes it suitable to be implanted. Thus, it may e.g. have perforations or through-holes, not shown, for allowing it to be securely attached to body tissues.

Figure 3:
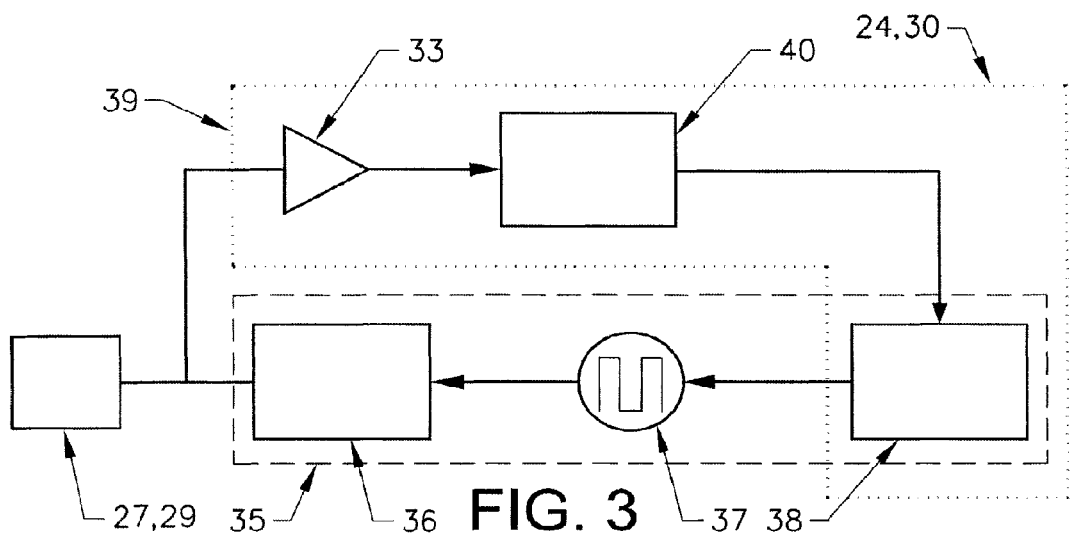
FIG. 3 shows a circuit diagram of an embodiment.

The driver circuits can be designed as is schematically illustrated in FIG. 3. FIG. 3 shows a circuit for both transmitting and receiving information, but it should be pointed out that the system of the invention can also be a "one way" system, so that the second part is solely a transmitter, and the first part is solely a receiver. The circuit shown in FIG. 3 is "generic", in that it may be used by either of the first and second part, with variations depending on whether or not both parts of the system should be able to both transit and receive information from the other part.

However, assuming a "two-way" system, as shown in FIG. 3, a capacitor plate 27, 29 is connected to a transmission stage 35 that includes a transmission output stage 36, which receives an input signal a wave or alternating electric signal from an oscillator circuit 37, e.g. a voltage controlled oscillator (VCO), with both the oscillator circuit 37 and the transmission output stage 36 both being controlled by a microcontroller 38 such as for commanding a special wave form and for modulating it, respectively.

The capacitor plate 27, 29 is also connected to a receiving stage 39 that includes an amplifier 33 which also functions as a bandpass filter. The amplifier provides 33 its output signal to a signal detector 40 which delivers the detected information signal to the microcontroller 38. The driver circuits for the external and internal capacitor plates can include either of the transmission and receiving stages 35, 39, or both of them, depending on the desired function. The microcontroller can, for example, be of the type PIC16F818, and it thus controls the transmission and receiving stage. For the "receive mode", the microcontroller converts the signal level received from the signal detector 35, and then suitably uses an ADC such the on-chip 8-bit ADC built into the PIC16F818.

As was shown in FIG. 1, in one embodiment, the second part of the system 20, i.e. including the external capacitor plate 27 and its driver circuits 24 and power supply 25 can be integrated in a device such as a wristwatch 45. However, a wristwatch is merely one example of a device in which the second part may be integrated; examples of other such devices are a necklace, a bracelet, a ring, an ear ring or a piercing ornament for the human body, or a traditional watch.

In FIG. 2, the driver circuits 30, the power supply 31 and the internal capacitor plate 29 are seen to be separate units, connected by electrical cabling. These components can also be integrated as a single unit, placed together inside a common enclosure or housing, which can be made from an electrically insulating material which forms the electrical insulation of the capacitor plate.

The communication channel or path having a capacitive coupling as described above should have constant impedance, which should be as small as possible in order to ensure that the communication signals are appropriately transferred. However, the capacitance of the capacitor used, having one capacitor plate 29 implanted in a patient's body may not stay constant, due to, for example, the fact that the plates 27, 29 can move in relation to each other, and that body functions in the tissues located between the capacitor plates can change. The frequency used for the communication should be substantially constant, if e.g. a carrier signal which is modulated is used or pulses of a definite frequency is used. Also, the frequency should suitably be as large as possible, in order to make the impedance small.

Figures 4, 5:
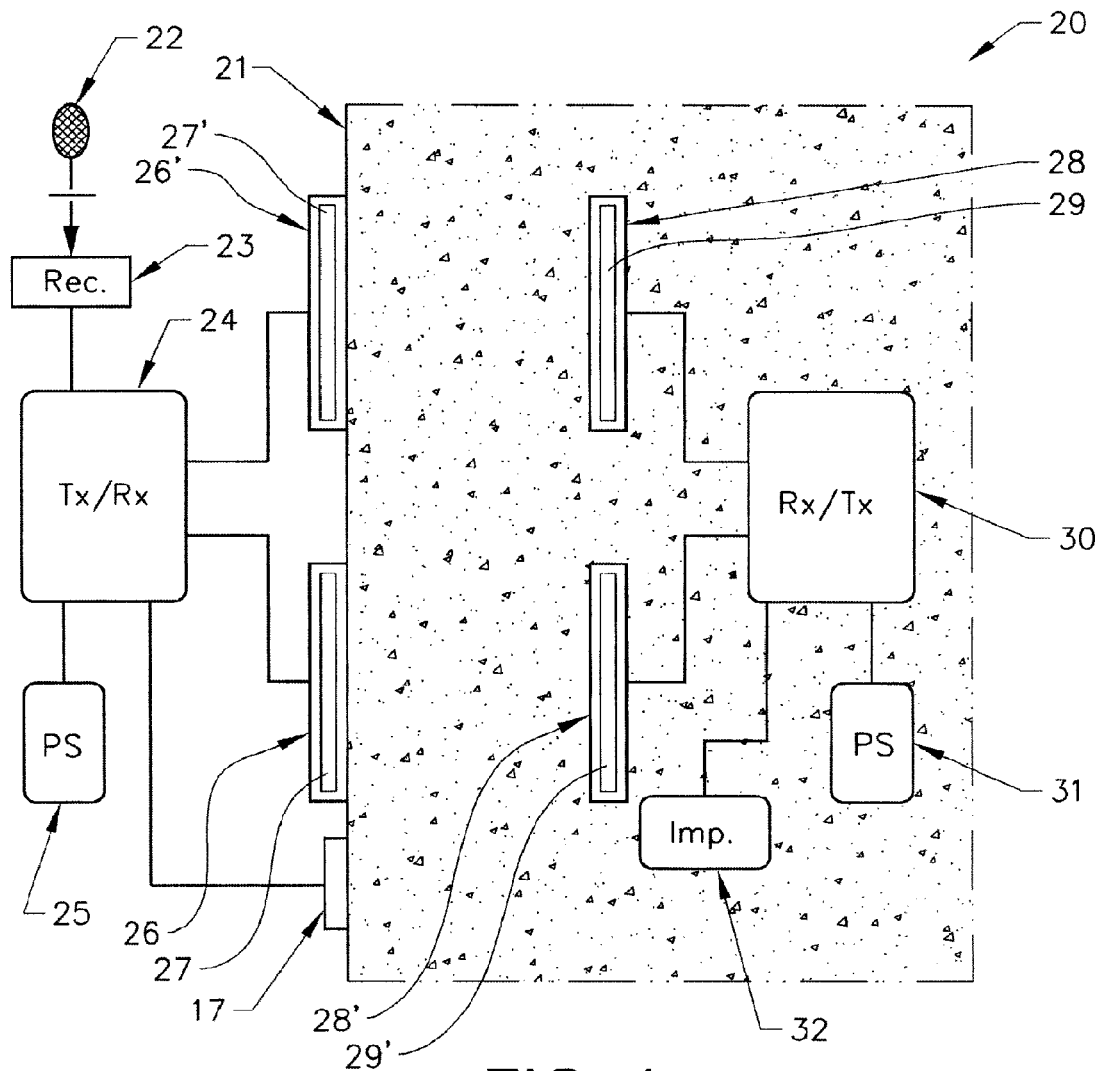
FIGS. 4 and 5 show block diagrams of further embodiments.

In order to improve the total capacitive coupling between the capacitor plates 27, 29, the plates can be "divided" to each include a first plate 27, 29 and a second plate 27', 29', as shown in FIG. 4, with the system 20 being essentially similar otherwise to that shown in FIG. 2. For transmitting a signal from one part of the system to the other part of the system, the two plates on the sending side can be then provided with signals which are the inverse of each other. Thus, e.g. the plate 27' can be provided with the direct signal and be denoted 27+ and the plate 27 can be provided with the inverted signal, then be denoted 27−. The inversion of signals can be easily achieved by arranging an inverter circuit in the transmission stage 21 of FIG. 2. In the receiving part, i.e. the first (implanted) part of the system, an inverter circuit having the opposite direction can be used. The internal capacitor plate must be configured in a similar and corresponding way, having one plate 29 for the direct signal and one plate 29' for the inverted signal.

The dual capacitor plates used in this case can for ease of positioning be configured as concentric circular fields, as shown in FIG. 5, at least one of which is annular. One capacitor portion 27+, 29+ can e.g. be a central circular field that is surrounded by an annular circular field 27−, 29−.

Various ways of communicating signals over the communication path involving a capacitive coupling can be conceived, considering the above mentioned conditions of the signal transmission; some possible methods will now be described.

In the simplest case, the signals used in the communication between the external and internal devices can e.g. be electric pulses, e.g. substantially rectangular pulses. However, since the communication of information in most case must be made with a high degree of security, a suitable coding of the information could be used. Hence, e.g. Manchester coding can be used.

Manchester encoding is a special case of binary phase shift keying where each bit of data is signified by at least one transition. The encoding is therefore self-clocking which makes accurate synchronization of the data stream possible. For example, a "1" can be represented by a transition from a high to a low level and a "0" can be represented by a transition from a low to a high electrical level. This means that in the derivative of the electrical signal, there are variations so that a "1" can be seen as a negative pulse and a "0" as a positive pulse. In the electrical signal there are also transitions between the two levels that do not represent any information but are necessary in order that the transitions representing information can be arranged in the electrical, such extra transitions thus inserted when sending two equal consecutive bits of information.

Figure 6:
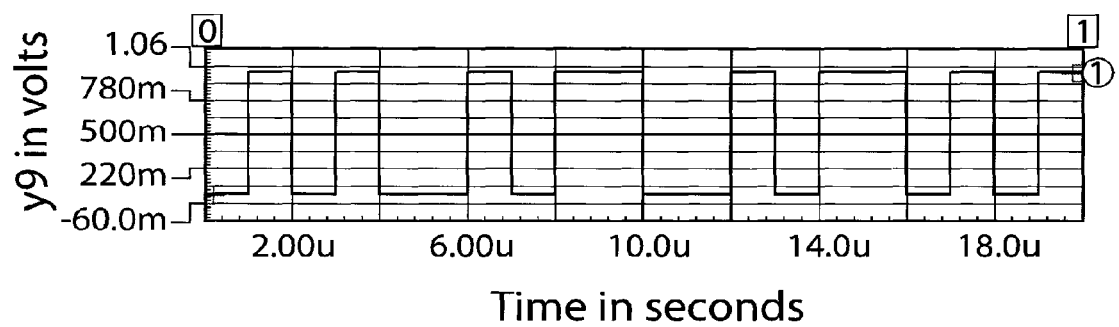
FIGS. 6-8 show various embodiments of communication.

For the case of simple pulse transmission, the transmitter output stage 36 and the oscillator 37 illustrated in the circuit diagram of FIG. 3 may not be required since the pulses can be generated directly in the microprocessor 38 and provided to the respective capacitor plate 27, 29. A typical Manchester encoded signal generated by a microcontroller is illustrated in the diagram of FIG. 6.

Figure 7:
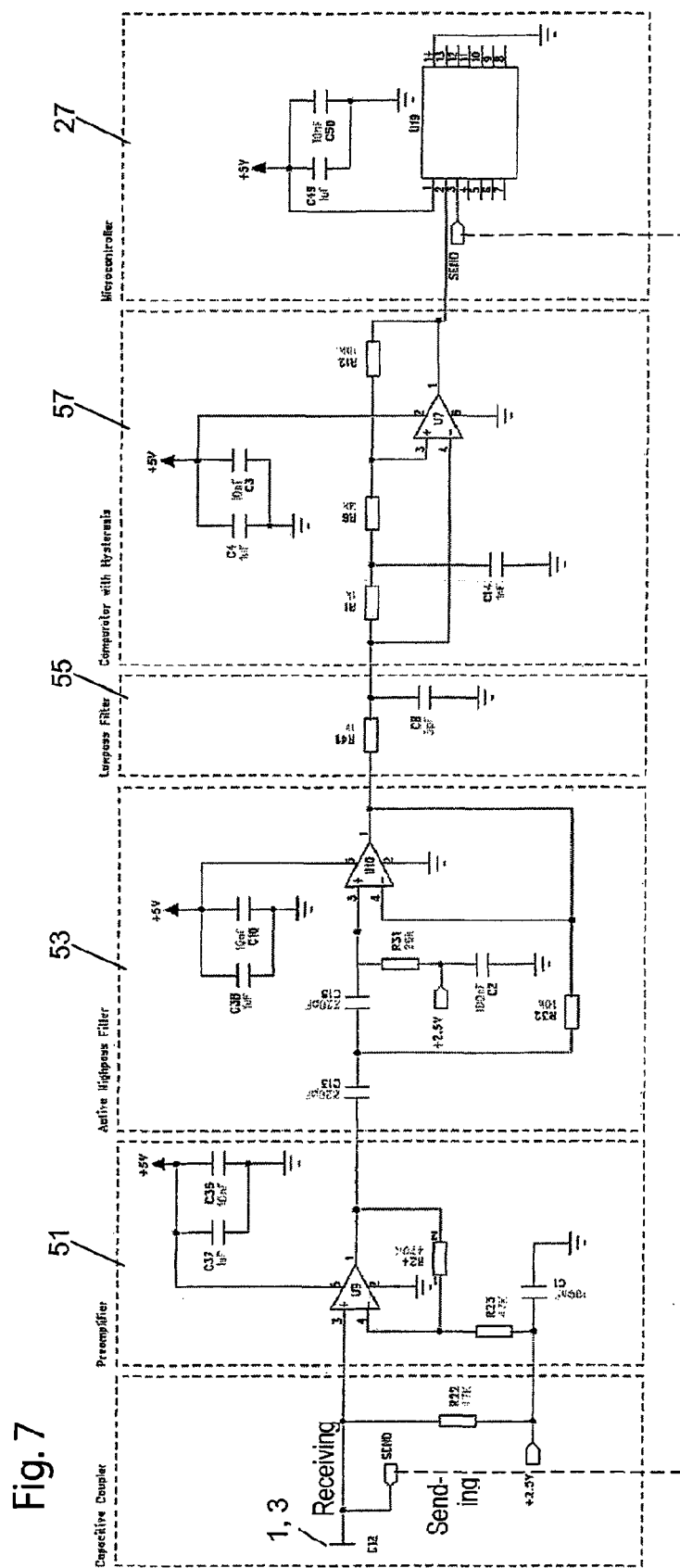

FIG. 7 is a circuit diagram of driver circuits 24, 30 comprising a transceiver that can be used in this case.

For receiving, the transmitted signal is picked up by the capacitor plate 27, 29. The DC level of the signal is by the resistor R22 pulled to 2.5V which is equal to VCC/2. The received signal is provided to a preamplifier stage 51 including an amplifier U9 before it is passed to filter stages. The amplifier has a high input impedance and a low bias current. The signal is then provided to a high pass filter stage 53 that is configured as a second order active high pass filter including an amplifier U10 as its active element. This filter stage removes low frequency interfering signals and noise. Then, the signal is passed to a low pass filter stage 55 being a passive filter of RC-type, comprising a resistor R41 and a capacitor C8 to remove high frequency noise.

The signal is then provided to a signal detector stage that here is designed as a comparator 57 stage having hysteresis. Thus, the received and filtered signal is fed to the inverting input of a comparator U7. The same signal is also first even more low pass filtered in a passive RC-filter including R41 and C14 and then fed to the non-inverting input of the comparator via a resistor R6. The resistor R6 and the feedback resistor R12 form the hysteresis feedback. The comparator U7 has hysteresis in order to output a square wave in Manchester code even if the signal drops down below the DC level. An example of a received and filter signal can be seen in FIG. 6b and the output from the comparator U7 in FIG. 6c.

The microcontroller U19 is used to decode the received Manchester stream into useful data. This is achieved by measuring the time between rising and falling edges. When a reception is initialized, the microcontroller receives a preamble consisting of the repeated pattern "10101010". Since the only transitions that occur in that pattern are the bit transitions the preamble can be used to synchronize the data, i.e. to form a clock signal. When synchronization has been accomplished, the microcontroller can begin to translate the Manchester stream into useful data.

Another method is to use amplitude modulation to transfer data. For instance, a carrier frequency can be on/off-modulated to output bursts of the electrical signal.

Figure 8:
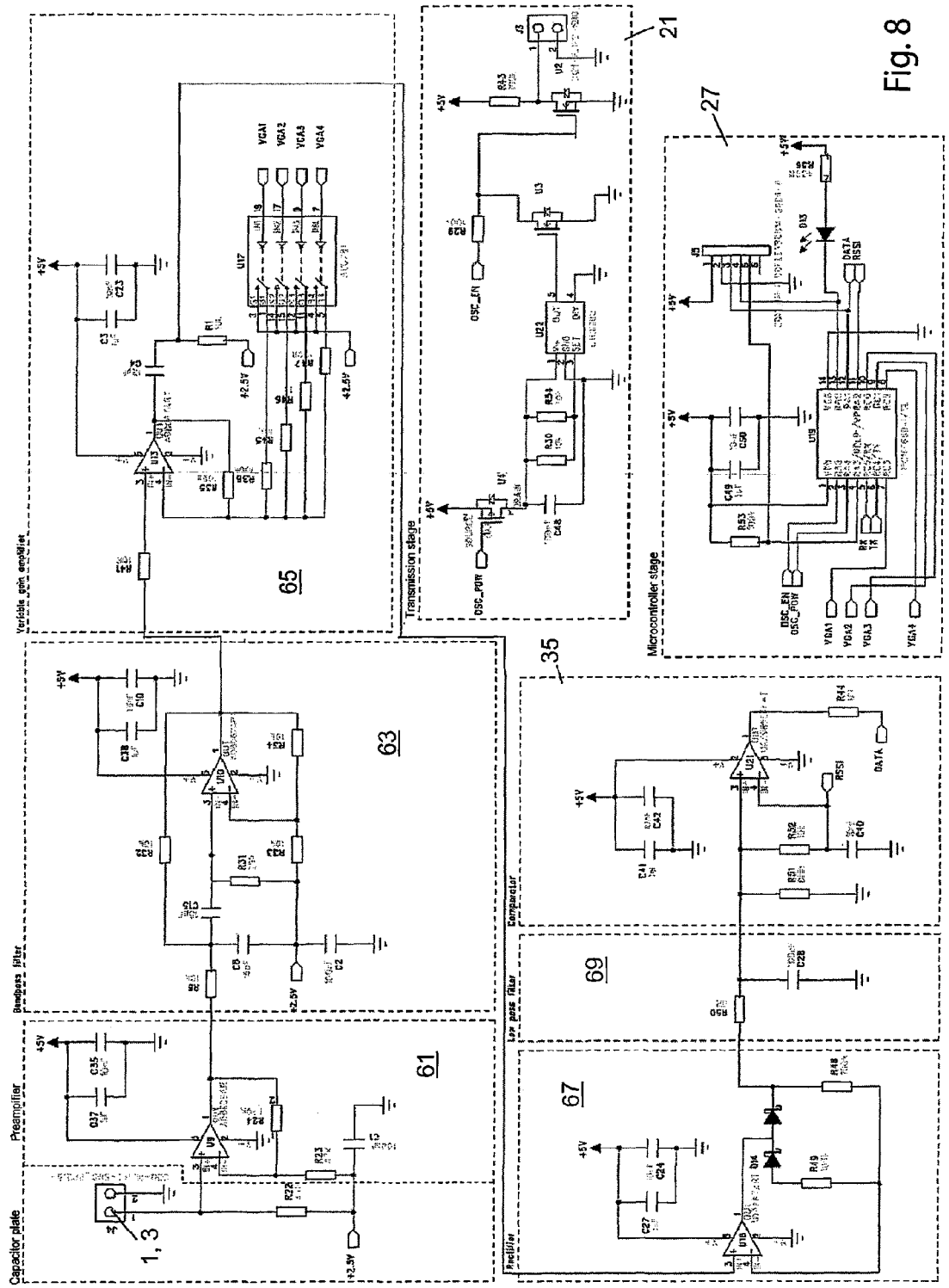

For this method, driver circuits like those illustrated in FIG. 8 may for instance be used. The transmission stage 21 has a signal generator U22 that can be enabled by a signal "OSC_POW" from the microcontroller U19 in the microcontroller stage, the signal opening a transistor U4. The signal generator U22 outputs a oscillatory signal having a frequency of about 1.4 MHz that is set by the resistors R30 and R54. The output from the signal generator U22 is fed to the gate of another transistor U3. Another signal "OSC_EN" from the microcontroller is used to modulate the amplitude of the signal by being provided the gate of a transistor U2. The transistor U2 and resistor R43 are provided to make it possible to transmit a voltage higher than 5V.

For receiving information, the transmitted signal is picked up by the capacitor plate connected to J4. The DC level of the received signal is by the resistor 22 pulled to 2.5V which is equal to VCC/2. The received is provided to a preamplifier stage 61 including an amplifier U9 having a high input impedance and a low bias current. The amplified signal is passed to a bandpass filter 63. The bandpass filter is a second order active band pass filter including an amplifier U10 as its active element.

The filtered signal is provided to a variable gain amplifier 65 including a non-inverting amplifier U13. A resistor connects the inverting input of the non-inverting amplifier to a reference voltage that can be chosen by setting an analogue switch U17. The gain of the variable gain amplifier 65 can therefore be set by the microcontroller 27 by control signals "VGA1-4". After having passed the variable gain amplifier, the signal is half-wave rectified in a rectifier stage 67 including an the amplifier U18 having two diodes D14 connected in its feedback loop. The rectified signal is by a passive low pass RC-filter 69 including a resistor R50 and a capacitor C28 to output a rectangular wave. The rectangular wave is high when the amplitude of the received signal is high or on and it is low when the amplitude is off or zero.

Finally, the desired signal is detected in a signal detector or comparator stage 35 by being provided to the non-inverting input of a comparator U21. The signal is also simultaneously low pass filtered by the RC-filter arranged by the resistor R52 and the capacitor C40 to provide an averaged signal to the inverting input. The signal "DATA" output from the comparator U21 is fed to the microcontroller 27 to decode the received data.

For the data reception to work properly in this case it may be important that the transmitted signal is balanced in the meaning that it is on and off for the same amount of time. The data can for that reason, also in this case, be encoded using Manchester code as described above.

A development of the simple amplitude modulation method using a carried that is switched on and off is the method called frequency shift keying (FSK). This modulation scheme represents a digital '0' with a first frequency and a '1' with a second, different frequency where these frequencies can be selected to be as large as possible. If possible, also rectangular waves can be used instead of sine waves to get a better transmission through the capacitive link.

In demodulating, in this case a received frequency is transformed into a '0' or '1'. This can be done using a phase locked loop (PLL), in particular a digital phase locked loop (DPLL). Such a digital demodulating circuit comprises a pfd or phase detector, a loop filter, a VCO counter and a decider. The phase detector looks on the incoming signal and compares it to the generated signal in the VCO counter. If any of the signals goes high before the other, this information is sent to the loop filter. The loop filter gets the information about which signal goes high first and translates this to a control signal for the VCO counter. This signal is the preset for the counter inside VCO counter. The VCO counter is a counter that always counts down and has a load and preset inputs. These inputs are controlled by the loop filter.

The decider is a unit or circuit which creates the data signal. This is done by looking at the preset signals and, depending on the value, choosing between a '0' and '1'.

Turning now to how energy is supplied to the parts of the inventive system 20, this has been hinted at in FIGS. 2 and 4, by means of the power supplies 25 and 31 shown there. The second part, i.e. the part which is adapted to be worn externally to the mammal body can be powered in a number of ways, such as batteries, rechargeable accumulators etc, but the power supply of the first part, i.e. the part which is adapted for implantation in a mammal body naturally presents a bigger challenge. In the following, a number of suitable alternative or complementary ways of powering the first part of the inventive system will be described.

The first part 10 of the system will also be referred to below as "the apparatus".

Figure 9:
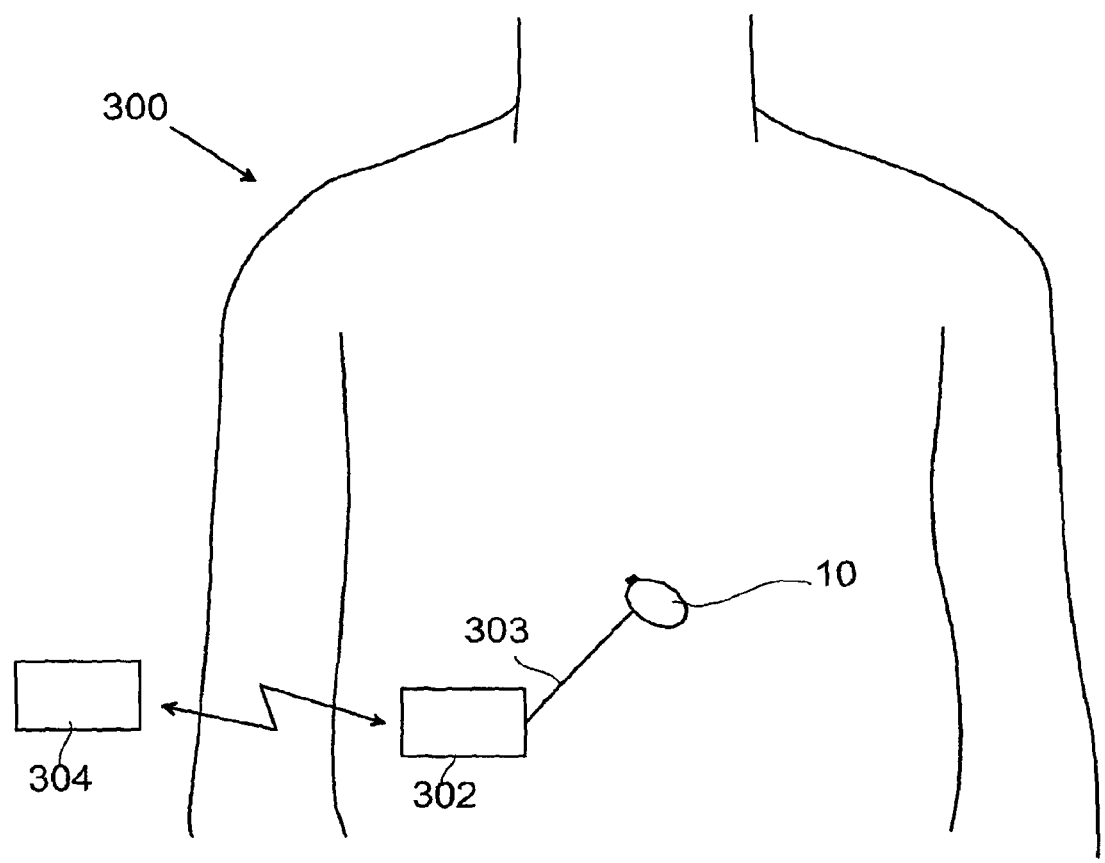
FIGS. 9-21 show embodiments of power sources for the first part of the invention.

FIG. 9 illustrates one embodiment of a system 300 for supplying the first part 10 of the present invention with energy. The first part 10 is, by way of example, in FIG. 9 shown as being placed in the abdomen of a patient; the implant which is to be controlled via the first part 10 is not shown in FIG. 9.

In one embodiment, an implantable energy-transforming device 302 is adapted to supply energy consuming components of the apparatus 10 with energy via a power supply line 303. An external energy-transmission device 304 for non-invasively energizing the apparatus 10 transmits energy to the implantable energy-transforming device 302 by at least one wireless energy signal. The implanted energy-transforming device 302 transforms energy from the wireless energy signal into electrical energy which is supplied via the power supply line 303.

The wireless energy signal may include a wave signal selected from the following: a sound wave signal, an ultrasound wave signal, an electromagnetic wave signal, an infrared light signal, a visible light signal, an ultra violet light signal, a laser light signal, a micro wave signal, a radio wave signal, an x-ray radiation signal and a gamma radiation signal. Alternatively, the wireless energy signal may include an electric or magnetic field, or a combined electric and magnetic field.

The wireless energy-transmission device 304 may transmit a carrier signal for carrying the wireless energy signal. Such a carrier signal may include digital, analogue or a combination of digital and analogue signals. In this case, the wireless energy signal includes an analogue or a digital signal, or a combination of an analogue and digital signal.

Generally speaking, the energy-transforming device 302 is provided for transforming wireless energy of a first form transmitted by the energy-transmission device 304 into energy of a second form, which typically is different from the energy of the first form. The implanted apparatus 10 is operable in response to the energy of the second form. The energy-transforming device 302 may directly power the apparatus with the second form energy, as the energy-transforming device 302 transforms the first form energy transmitted by the energy-transmission device 304 into the second form energy. The system may further include an implantable accumulator, wherein the second form energy is used at least partly to charge the accumulator.

Alternatively, the wireless energy transmitted by the energy-transmission device 304 may be used to directly power the apparatus 10, as the wireless energy is being transmitted by the energy-transmission device 304. Where the system comprises an operation device for operating the apparatus, as will be described below, the wireless energy transmitted by the energy-transmission device 304 may be used to directly power the operation device to create kinetic energy for the operation of the apparatus.

The wireless energy of the first form may comprise sound waves and the energy-transforming device 302 may include a piezo-electric element for transforming the sound waves into electric energy. The energy of the second form may comprise electric energy in the form of a direct current or pulsating direct current, or a combination of a direct current and pulsating direct current, or an alternating current or a combination of a direct and alternating current. Normally, the apparatus comprises electric components that are energized with electrical energy. Other implantable electric components of the system may be at least one voltage level guard or at least one constant current guard connected with the electric components of the apparatus.

Optionally, one of the energy of the first form and the energy of the second form may comprise magnetic energy, kinetic energy, sound energy, chemical energy, radiant energy, electromagnetic energy, photo energy, nuclear energy or thermal energy. Preferably, one of the energy of the first form and the energy of the second form is non-magnetic, non-kinetic, non-chemical, non-sonic, non-nuclear or non-thermal.

The energy-transmission device may be controlled from outside the patient's body to release electromagnetic wireless energy, and the released electromagnetic wireless energy is used for operating the apparatus. Alternatively, the energy-transmission device is controlled from outside the patient's body to release non-magnetic wireless energy, and the released non-magnetic wireless energy is used for operating the apparatus. Naturally, the energy-transmission device can also be controlled by the communication between the first 10 and the second parts 12 of the invention.

The external energy-transmission device 304 can also, in one embodiment, include a wireless remote control having an external signal transmitter for transmitting a wireless control signal for non-invasively controlling the apparatus. The control signal is received by an implanted signal receiver which may be incorporated in the implanted energy-transforming device 302 or be separate there from.

The wireless control signal may include a frequency, amplitude, or phase modulated signal or a combination thereof. Alternatively, the wireless control signal includes an analogue or a digital signal, or a combination of an analogue and digital signal. Alternatively, the wireless control signal comprises an electric or magnetic field, or a combined electric and magnetic field.

The wireless remote control may transmit a carrier signal for carrying the wireless control signal. Such a carrier signal may include digital, analogue or a combination of digital and analogue signals. Where the control signal includes an analogue or a digital signal, or a combination of an analogue and digital signal, the wireless remote control preferably transmits an electromagnetic carrier wave signal for carrying the digital or analogue control signals.

Figure 10:
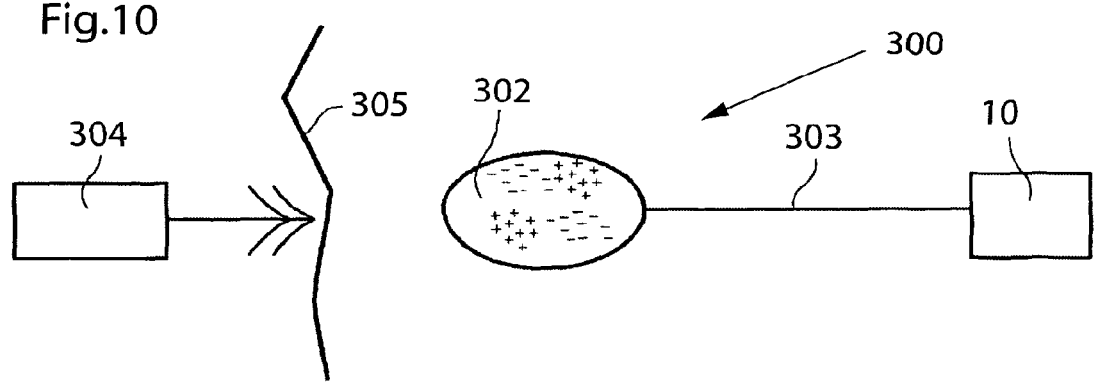

FIG. 10 illustrates the system of FIG. 9 in the form of a more generalized block diagram showing the apparatus 10, the energy-transforming device 302 powering the apparatus 10 via power supply line 303, and the external energy-transmission device 304, The patient's skin 305, generally shown by a vertical line, separates the interior of the patient to the right of the line from the exterior to the left of the line.

Figure 11:
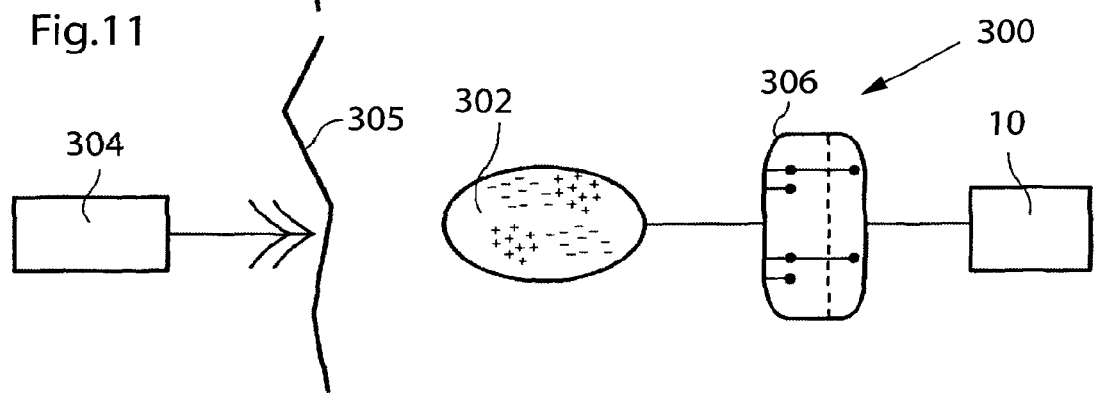

FIG. 11 shows an embodiment of the invention identical to that of FIG. 10, except that a reversing device in the form of an electric switch 306 operable for example by polarized energy also is implanted in the patient for reversing the apparatus 10. When the switch is operated by polarized energy the wireless remote control of the external energy-transmission device 304 transmits a wireless signal that carries polarized energy and the implanted energy-transforming device 302 transforms the wireless polarized energy into a polarized current for operating the electric switch 306. When the polarity of the current is shifted by the implanted energy-transforming device 302 the electric switch 306 reverses the function performed by the apparatus 10.

In all of the embodiments described herein, the energy-transforming device 302 may include a rechargeable accumulator like a battery or a capacitor to be charged by the wireless energy and supplies energy for any energy consuming part of the system.

Figure 12:
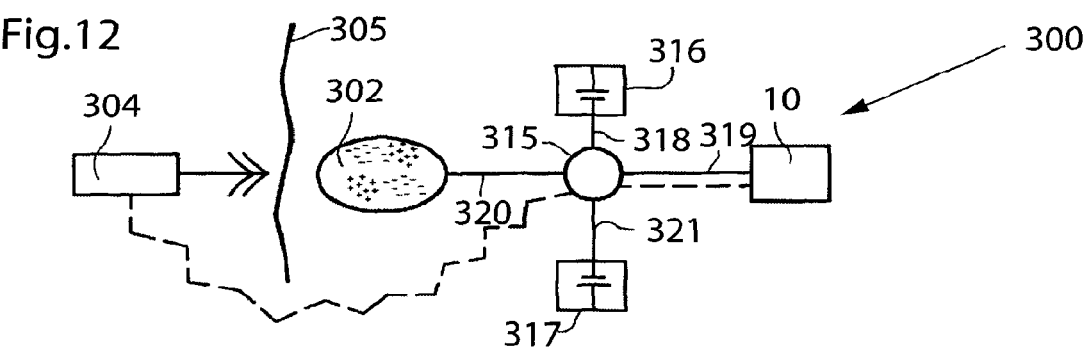

FIG. 12 shows an embodiment of the invention comprising the external energy-transmission device 304, the apparatus 10, the implanted energy-transforming device 302, an implanted internal control unit 315 controlled by the wireless remote control of the external energy-transmission device 304, an implanted accumulator 316 and an implanted capacitor 317.

The internal control unit 315 arranges storage of electric energy received from the implanted energy-transforming device 302 in the accumulator 316, which supplies energy to the apparatus 10. In response to a control signal from the wireless remote control of the external energy-transmission device 304, the internal control unit 315 either releases electric energy from the accumulator 316 and transfers the released energy via power lines 318 and 319, or directly transfers electric energy from the implanted energy-transforming device 302 via a power line 320, the capacitor 317, which stabilizes the electric current, a power line 321 and the power line 319, for the operation of the apparatus 10.

The internal control unit is preferably programmable from outside the patient's body. In a preferred embodiment, the internal control unit is programmed to regulate the apparatus 10 according to a pre-programmed time-schedule or to input from any sensor sensing any possible physical parameter of the patient or any functional parameter of the system.

In accordance with an alternative, the capacitor 317 in the embodiment of FIG. 12 may be omitted. In accordance with another alternative, the accumulator 316 in this embodiment may be omitted.

Figure 13:
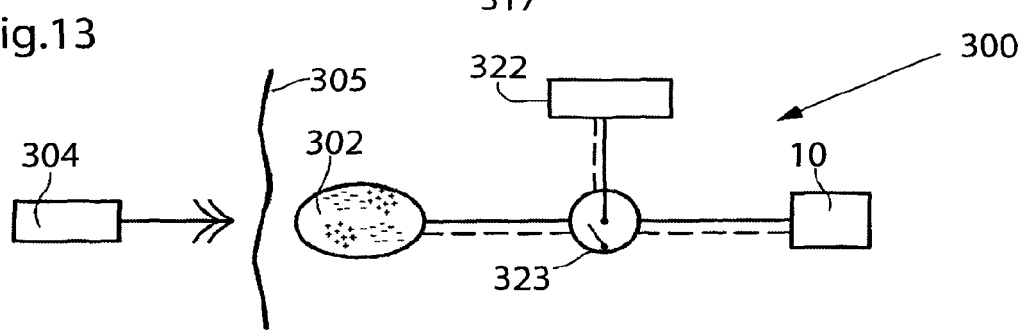

FIG. 13 shows an embodiment of the invention identical to that of FIG. 10, except that a battery 322 for supplying energy for the operation of the apparatus 10 and an electric switch 323 for switching the operation of the apparatus 10 are also implanted in the patient. The electric switch 323 may be controlled by the remote control and may also be operated by the energy supplied by the implanted energy-transforming device 302 to switch from an off mode, in which the battery 322 is not in use, to an on mode, in which the battery 322 supplies energy for the operation of the apparatus 10.

Figure 14:
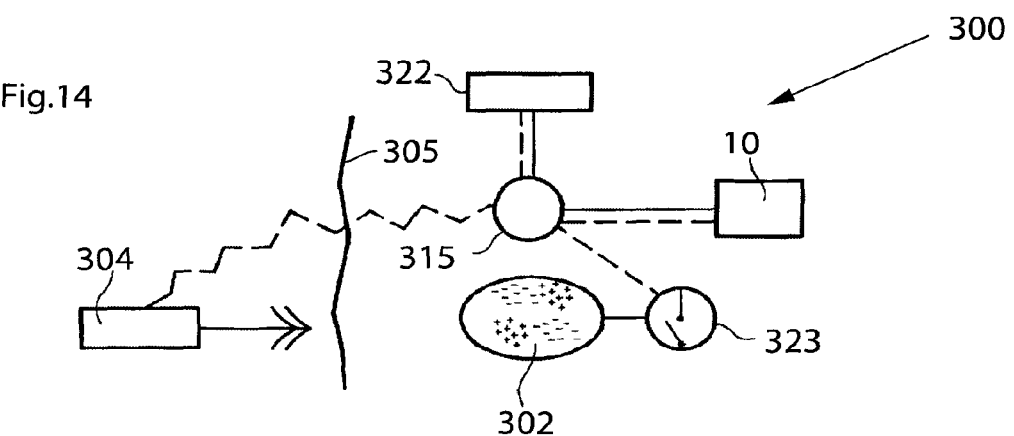

FIG. 14 shows an embodiment of the invention identical to that of FIG. 13, except that an internal control unit 315 controllable by a wireless remote control of the external energy-transmission device 304 also is implanted in the patient. In this case, the electric switch 323 is operated by the energy supplied by the implanted energy-transforming device 302 to switch from an off mode, in which the wireless remote control is prevented from controlling the internal control unit 315 and the battery is not in use, to a standby mode, in which the remote control is permitted to control the internal control unit 315 to release electric energy from the battery 322 for the operation of the apparatus 10.

Figure 15:
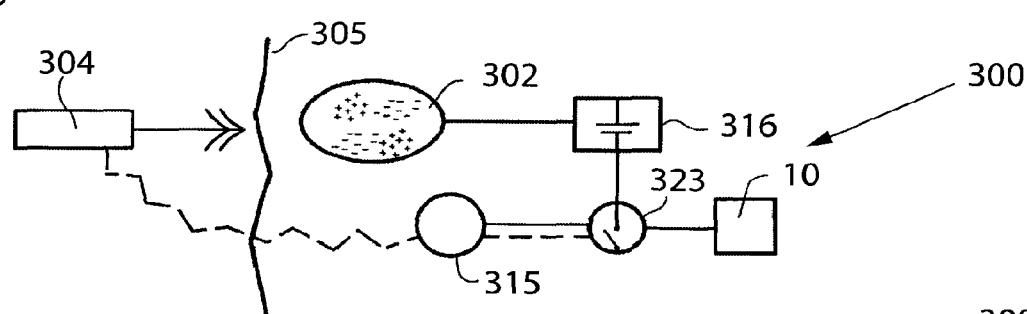

FIG. 15 shows an embodiment of the invention identical to that of FIG. 14, except that an accumulator 316 is substituted for the battery 322 and the implanted components are interconnected differently. In this case, the accumulator 316 stores energy from the implanted energy-transforming device 302. In response to a control signal from the wireless remote control of the external energy-transmission device 304, the internal control unit 315 controls the electric switch 323 to switch from an off mode, in which the accumulator 316 is not in use, to an on mode, in which the accumulator 316 supplies energy for the operation of the apparatus 10. The accumulator may be combined with or replaced by a capacitor.

Figure 16:
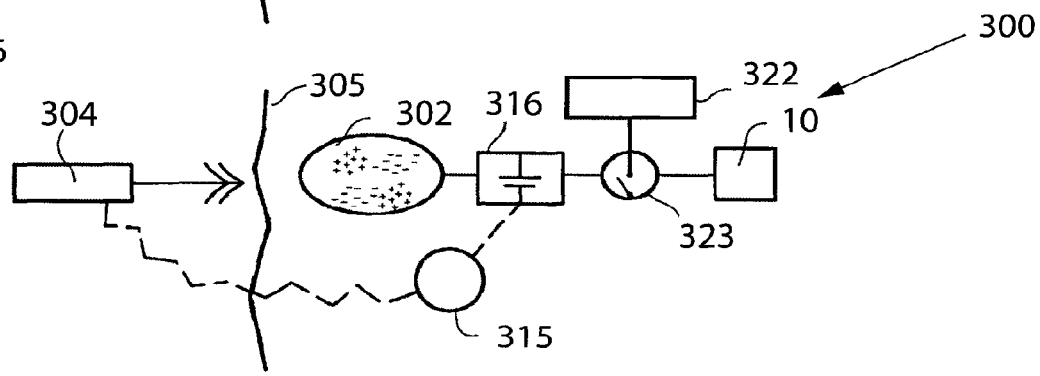

FIG. 16 shows an embodiment of the invention identical to that of FIG. 15, except that a battery 322 also is implanted in the patient and the implanted components are interconnected differently. In response to a control signal from a wireless remote control of the external energy-transmission device 304, the internal control unit 315 controls the accumulator 316 to deliver energy for operating the electric switch 323 to switch from an off mode, in which the battery 322 is not in use, to an on mode, in which the battery 322 supplies electric energy for the operation of the apparatus 10.

Alternatively, the electric switch 323 may be operated by energy supplied by the accumulator 316 to switch from an off mode, in which the wireless remote control is prevented from controlling the battery 322 to supply electric energy and is not in use, to a standby mode, in which the wireless remote control is permitted to control the battery 322 to supply electric energy for the operation of the apparatus 10.

It should be understood that the switch 323 and all other switches in this application should be interpreted in its broadest embodiment. This means a transistor, MCU, MCPU, ASIC, FPGA or a DA converter or any other electronic component or circuit that may switch the power on and off. Preferably the switch is controlled from outside the body, or alternatively by an implanted internal control unit.

Figure 17:
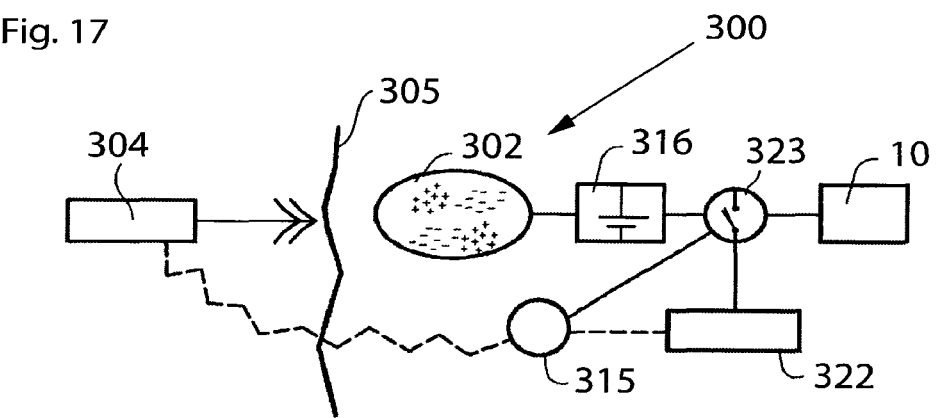

FIG. 17 shows an embodiment of the invention identical to that of FIG. 14 except that the implanted components are interconnected differently. Thus, in this case, the internal control unit 315 is powered by the battery 322 when the accumulator 316, suitably a capacitor, activates the electric switch 323 to switch to an "on" mode. When the electric switch 323 is in its "on" mode, the internal control unit 315 is permitted to control the battery 322 to supply, or not supply, energy for the operation of the apparatus 10.

Figure 18:
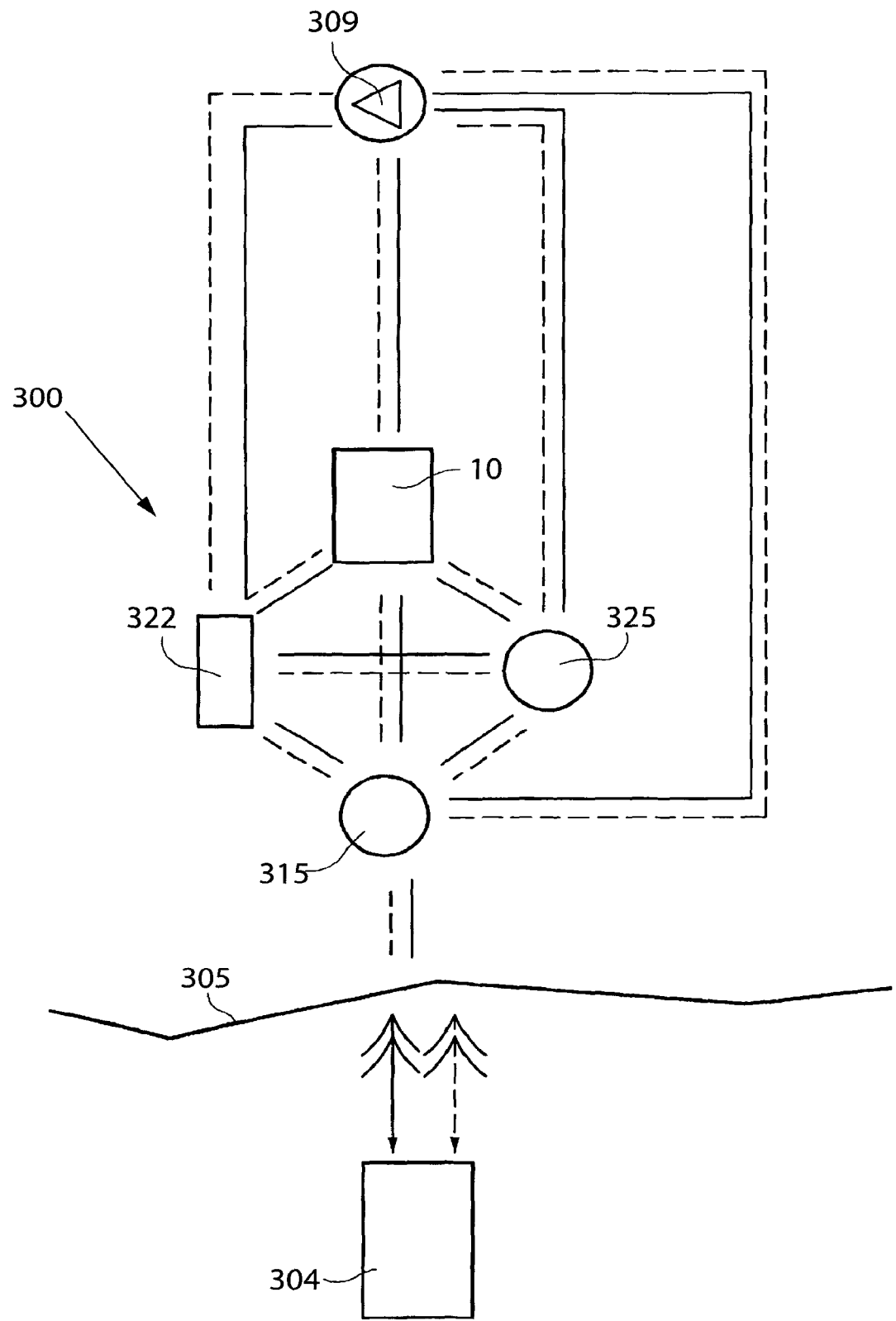

FIG. 18 schematically shows conceivable combinations of implanted components of the apparatus for achieving various communication options. Basically, there is the apparatus 10, the internal control unit 315, an optional component 309, and the external energy-transmission device 304 including the external wireless remote control. As already described above, a wireless remote control transmits a control signal which is received by the internal control unit 315, which in turn controls the various implanted components of the apparatus.

The internal control unit 315, or alternatively the external wireless remote control of the external energy-transmission device 304, may control the apparatus 10 in response to signals from the sensor 325. A transceiver may be combined with the sensor 325 for sending information on the sensed physical parameter to the external wireless remote control. The wireless remote control may comprise a signal transmitter or transceiver and the internal control unit 315 may comprise a signal receiver or transceiver.

Alternatively, the wireless remote control may comprise a signal receiver or transceiver and the internal control unit 315 may comprise a signal transmitter or transceiver. The above transceivers, transmitters and receivers may be used for sending information or data related to the apparatus 10 from inside the patient's body to the outside thereof.

Where the battery 322 for powering the apparatus 10 is implanted, information related to the charging of the battery 322 may be fed back. To be more precise, when charging a battery or accumulator with energy, feedback information related to said charging process is sent and the energy supply is changed accordingly. This information is suitably sent via the communication between the first and second parts of the inventive system.

An internal energy receiver can be adapted to directly or indirectly supply received energy to the energy consuming components of the apparatus 10 via a switch 326. An energy balance is determined between the energy received by the internal energy receiver 302 and the energy used for the apparatus 10, and the transmission of wireless energy is then controlled based on the determined energy balance. The energy balance thus provides an accurate indication of the correct amount of energy needed, which is sufficient to operate the apparatus 10 properly, but without causing undue temperature rise.

In FIGS. 10-17, the patient's skin is indicated by a vertical line 305. Here, the energy receiver comprises an energy-transforming device 302 located inside the patient, preferably just beneath the patient's skin 305. Generally speaking, the implanted energy-transforming device 302 may be placed in the abdomen, thorax, muscle fascia (e.g. in the abdominal wall), subcutaneously, or at any other suitable location. The implanted energy-transforming device 302 is adapted to receive wireless energy E transmitted from the external energy-source 304a provided in an external energy-transmission device 304 located outside the patient's skin 305 in the vicinity of the implanted energy-transforming device 302.

As is well known in the art, the wireless energy E may generally be transferred by means of any suitable Transcutaneous Energy Transfer (TET) device, such as a device including a primary coil arranged in the external energy source 304a and an adjacent secondary coil arranged in the implanted energy-transforming device 302. When an electric current is fed through the primary coil, energy in the form of a voltage is induced in the secondary coil which can be used to power the implanted energy consuming components of the apparatus, e.g. after storing the incoming energy in an implanted energy source, such as a rechargeable battery or a capacitor.

However, the present invention is generally not limited to any particular energy transfer technique, TET devices or energy sources, and any kind of wireless energy may be used. The amount of energy received by the implanted energy receiver may be compared with the energy used by the implanted components of the apparatus. The term "energy used" is then understood to include also energy stored by implanted components of the apparatus.

A control device includes an external control unit that controls the external energy source 304a based on the determined energy balance to regulate the amount of transferred energy. In order to transfer the correct amount of energy, the energy balance and the required amount of energy is determined by means of a determination device including an implanted internal control unit 315 connected between the switch 326 and the apparatus 10. The internal control unit 315 may thus be arranged to receive various measurements obtained by suitable sensors or the like, not shown, measuring certain characteristics of the apparatus 10, somehow reflecting the required amount of energy needed for proper operation of the apparatus 10.

Moreover, the current condition of the patient may also be detected by means of suitable measuring devices or sensors, in order to provide parameters reflecting the patient's condition. Hence, such characteristics and/or parameters may be related to the current state of the apparatus 10, such as power consumption, operational mode and temperature, as well as the patient's condition reflected by parameters such as; body temperature, blood pressure, heartbeats and breathing. Other kinds of physical parameters of the patient and functional parameters of the device are described elsewhere.

Furthermore, an energy source in the form of an accumulator 316 may optionally be connected to the implanted energy-transforming device 302 via the control unit 315 for accumulating received energy for later use by the apparatus 10. Alternatively or additionally, characteristics of such an accumulator, also reflecting the required amount of energy, may be measured as well. The accumulator may be replaced by a rechargeable battery, and the measured characteristics may be related to the current state of the battery, any electrical parameter such as energy consumption voltage, temperature, etc. In order to provide sufficient voltage and current to the apparatus 10, and also to avoid excessive heating, it is clearly understood that the battery should be charged optimally by receiving a correct amount of energy from the implanted energy-transforming device 302, i.e. not too little or too much. The accumulator may also be a capacitor with corresponding characteristics.

For example, battery characteristics may be measured on a regular basis to determine the current state of the battery, which then may be stored as state information in a suitable storage means in the internal control unit 315. Thus, whenever new measurements are made, the stored battery state information can be updated accordingly. In this way, the state of the battery can be "calibrated" by transferring a correct amount of energy, so as to maintain the battery in an optimal condition.

Thus, the internal control unit 315 of the determination device is adapted to determine the energy balance and/or the currently required amount of energy, (either energy per time unit or accumulated energy) based on measurements made by the above-mentioned sensors or measuring devices of the apparatus 10, or the patient, or an implanted energy source if used, or any combination thereof. The internal control unit 315 is further connected to an internal signal transmitter 327, arranged to transmit a control signal reflecting the determined required amount of energy, to an external signal receiver 304c connected to the external control unit 304b. The amount of energy transmitted from the external energy source 304a may then be regulated in response to the received control signal.

Alternatively, the determination device may include the external control unit 304b. In this alternative, sensor measurements can be transmitted directly to the external control unit 304b wherein the energy balance and/or the currently required amount of energy can be determined by the external control unit 304b, thus integrating the above-described function of the internal control unit 315 in the external control unit 304b. In that case, the internal control unit 315 can be omitted and the sensor measurements are supplied directly to the internal signal transmitter 327 which sends the measurements over to the external signal receiver 304c and the external control unit 304b. The energy balance and the currently required amount of energy can then be determined by the external control unit 304b based on those sensor measurements.

Hence, the present solution can employ the feedback of information indicating the required energy, which is more efficient than many other solutions since it is based on the actual use of energy that is compared to the received energy, e.g. with respect to the amount of energy, the energy difference, or the energy receiving rate as compared to the energy rate used by implanted energy consuming components of the apparatus. The apparatus may use the received energy either for consuming or for storing the energy in an implanted energy source or the like. The different parameters discussed above would thus be used if relevant and needed and then as a tool for determining the actual energy balance. However, such parameters may also be needed per se for any actions taken internally to specifically operate the apparatus.

Thus, the feedback information may be transferred either by a separate communication system including receivers and transmitters or may be integrated in the energy system, or by means of the communication between the first and the second part of the system. In accordance with one embodiment of the present invention, such an integrated information feedback and energy system comprises an implantable internal energy receiver for receiving wireless energy, the energy receiver having an internal first coil and a first electronic circuit connected to the first coil, and an external energy transmitter for transmitting wireless energy, the energy transmitter having an external second coil and a second electronic circuit connected to the second coil.

The external second coil of the energy transmitter transmits wireless energy which is received by the first coil of the energy receiver. This embodiment of the inventive system further comprises a power switch for switching the connection of the internal first coil to the first electronic circuit on and off, such that feedback information related to the charging of the first coil is received by the external energy transmitter in the form of an impedance variation in the load of the external second coil, when the power switch switches the connection of the internal first coil to the first electronic circuit on and off. In implementing this embodiment of the system, the switch is either separate and controlled by the internal control unit 315, or integrated in the internal control unit 315. It should be understood that the switch 326 should be interpreted in its broadest embodiment. This means a transistor, MCU, MCPU, ASIC FPGA or a DA converter or any other electronic component or circuit that may switch the power on and off.

To conclude, this embodiment of the energy supply arrangement may operate basically in the following manner: The energy balance is first determined by the internal control unit 315 of the determination device. A control signal reflecting the required amount of energy is also created by the internal control unit 315, and the control signal is transmitted from the internal signal transmitter 327 to the external signal receiver 304c. Alternatively, the energy balance can be determined by the external control unit 304b instead depending on the implementation, as mentioned above. In that case, the control signal may carry measurement results from various sensors.

The amount of energy emitted from the external energy source 304a can then be regulated by the external control unit 304b, based on the determined energy balance, e.g. in response to the received control signal. This process may be repeated intermittently at certain intervals during ongoing energy transfer, or may be executed on a more or less continuous basis during the energy transfer.

The amount of transferred energy can generally be regulated by adjusting various transmission parameters in the external energy source 304a, such as voltage, current, amplitude, wave frequency and pulse characteristics.

This system may also be used to obtain information about the coupling factors between the coils in a TET system even to calibrate the system both to find an optimal place for the external coil in relation to the internal coil and to optimize energy transfer. Simply comparing in this case the amount of energy transferred with the amount of energy received. For example if the external coil is moved the coupling factor may vary and correctly displayed movements could cause the external coil to find the optimal place for energy transfer. Preferably, the external coil is adapted to calibrate the amount of transferred energy to achieve the feedback information in the determination device, before the coupling factor is maximized.

This coupling factor information may also be used as a feedback during energy transfer. In such a case, the energy system of the present invention comprises an implantable internal energy receiver for receiving wireless energy, the energy receiver having an internal first coil and a first electronic circuit connected to the first coil, and a external energy transmitter for transmitting wireless energy, the energy transmitter having an external second coil and a second electronic circuit connected to the second coil.

The external second coil of the energy transmitter transmits wireless energy which is received by the first coil of the energy receiver. This system further comprises a feedback device for communicating out the amount of energy received in the first coil as a feedback information, and wherein the second electronic circuit includes a determination device for receiving the feedback information and for comparing the amount of transferred energy by the second coil with the feedback information related to the amount of energy received in the first coil to obtain the coupling factor between the first and second coils. The energy transmitter may regulate the transmitted energy in response to the obtained coupling factor.

Figure 19:
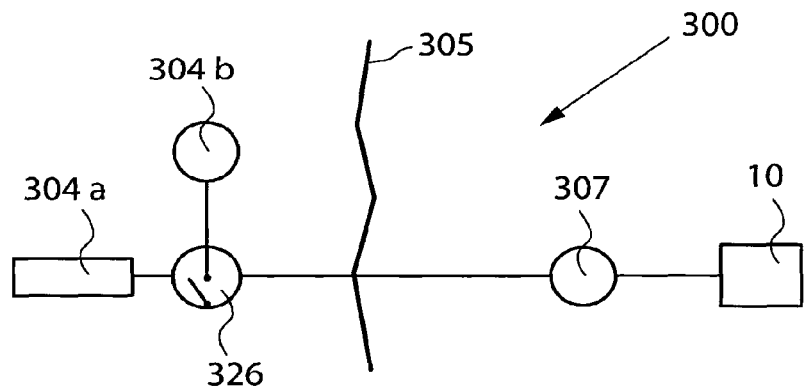
Figure 20:
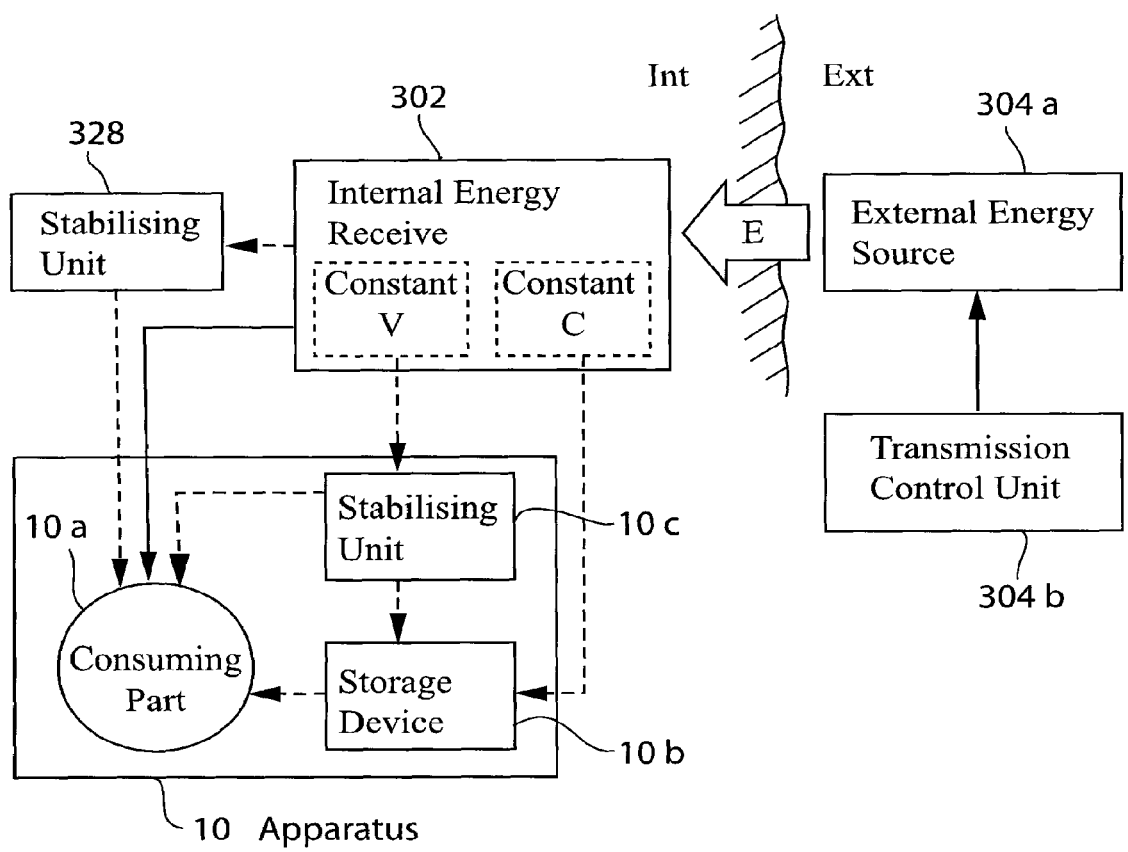

With reference to FIG. 19, although wireless transfer of energy for operating the apparatus has been described above to enable non-invasive operation, it will be appreciated that the apparatus can be operated with wire bound energy as well. Such an example is shown in FIG. 20, wherein an external switch 326 is interconnected between the external energy source 304a and an operation device, such as an electric motor 307 operating the apparatus 10. An external control unit 304b controls the operation of the external switch 326 to effect proper operation of the apparatus 10.

FIG. 20 illustrates different embodiments for how received energy can be supplied to and used by the apparatus 10. Similar to the example of FIG. 19, an internal energy receiver 302 receives wireless energy E from an external energy source 304a which is controlled by a transmission control unit 304b. The internal energy receiver 302 may comprise a constant voltage circuit, indicated as a dashed box "constant V" in the figure, for supplying energy at constant voltage to the apparatus 10. The internal energy receiver 302 may further comprise a constant current circuit, indicated as a dashed box "constant C" in the figure, for supplying energy at constant current to the apparatus 10.

The apparatus 10 comprises an energy consuming part 10a, that requires energy for its electrical operation. The apparatus 10 may further comprise an energy storage device 10b for storing energy supplied from the internal energy receiver 302. Thus, the supplied energy may be directly consumed by the energy consuming part 10a, or stored by the energy storage device 10b, or the supplied energy may be partly consumed and partly stored. The apparatus 10 may further comprise an energy stabilizing unit 10c for stabilizing the energy supplied from the internal energy receiver 302. Thus, the energy may be supplied in a fluctuating manner such that it may be necessary to stabilize the energy before consumed or stored.

The energy supplied from the internal energy receiver 302 may further be accumulated and/or stabilized by a separate energy stabilizing unit 328 located outside the apparatus 10, before being consumed and/or stored by the apparatus 10. Alternatively, the energy stabilizing unit 328 may be integrated in the internal energy receiver 302. In either case, the energy stabilizing unit 328 may comprise a constant voltage circuit and/or a constant current circuit.

It should be noted that FIG. 19 and FIG. 20 illustrate some possible but non-limiting implementation options regarding how the various shown functional components and elements can be arranged and connected to each other. However, the skilled person will readily appreciate that many variations and modifications can be made within the scope of the present invention.

Figure 21:
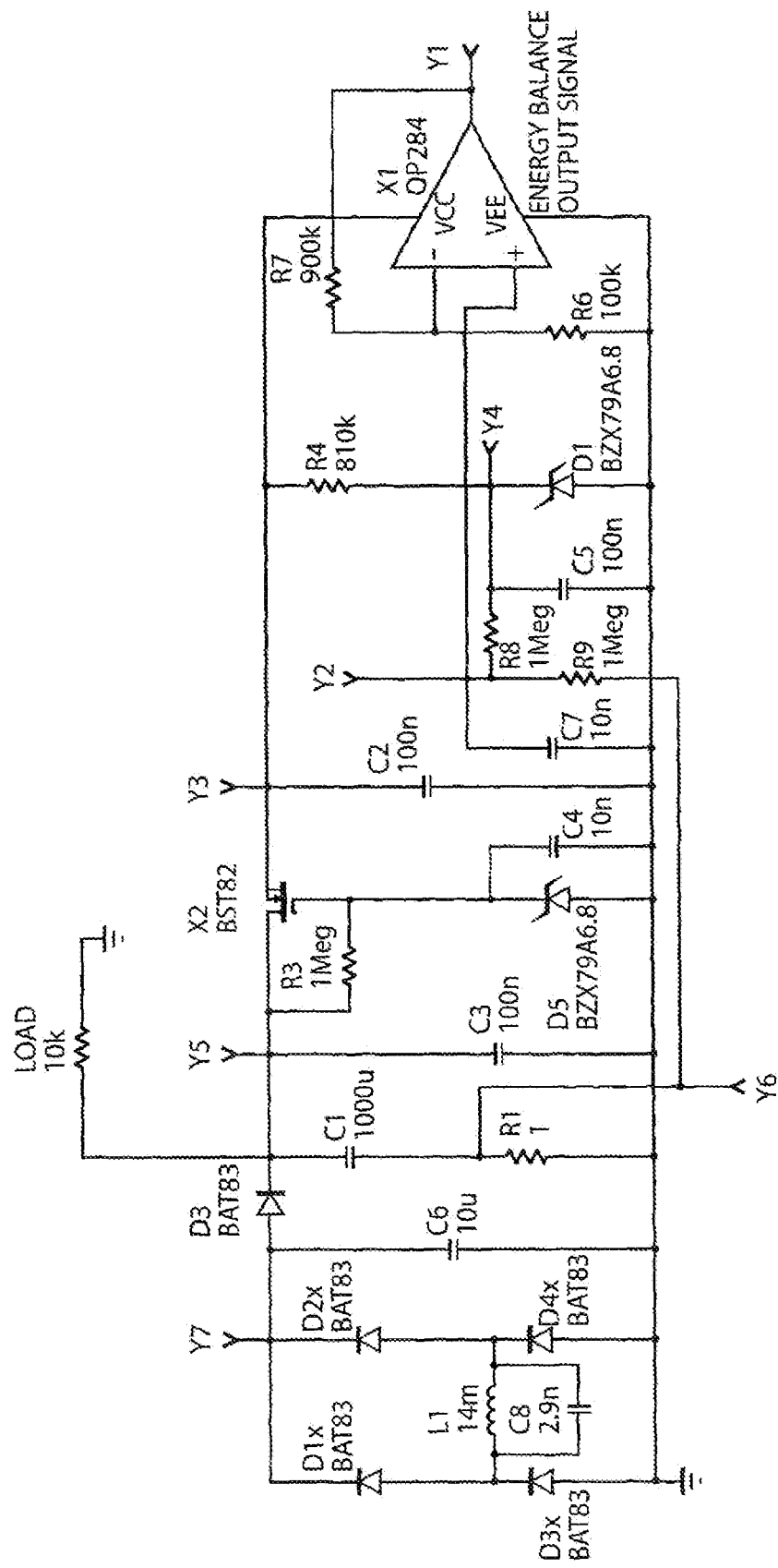

FIG. 21 schematically shows an energy balance measuring circuit of one of the proposed designs of the system for controlling transmission of wireless energy, or energy balance control system. The circuit has an output signal centered on 2.5V and proportionally related to the energy imbalance. The derivative of this signal shows if the value goes up and down and how fast such a change takes place. If the amount of received energy is lower than the energy used by implanted components of the apparatus, more energy is transferred and thus charged into the energy source.

The output signal from the circuit is typically feed to an A/D converter and converted into a digital format. The digital information can then be sent to the external energy-transmission device allowing it to adjust the level of the transmitted energy. Another possibility is to have a completely analog system that uses comparators comparing the energy balance level with certain maximum and minimum thresholds sending information to external energy-transmission device if the balance drifts out of the max/min window.

The schematic FIG. 21 shows a circuit implementation for a system that transfers energy to the implanted energy components of the apparatus of the present invention from outside of the patient's body using inductive energy transfer. An inductive energy transfer system typically uses an external transmitting coil and an internal receiving coil.

The implementation of the general concept of energy balance and the way the information is transmitted to the external energy transmitter can of course be implemented in numerous different ways. The schematic FIG. 23 and the above described method of evaluating and transmitting the information should only be regarded as examples of how to implement the control system.

Circuit Details

In FIG. 21 the symbols Y1, Y2, Y3 and so on symbolize test points within the circuit. The components in the diagram and their respective values are values that work in this particular implementation which of course is only one of an infinite number of possible design solutions.

Energy to power the circuit is received by the energy receiving coil L1. Energy to implanted components is transmitted in this particular case at a frequency of 25 kHz. The energy balance output signal is present at test point Y1.

Those skilled in the art will realize that the above various embodiments of the system could be combined in many different ways. For example, the electric switch 306 of FIG. 21 could be incorporated in any of the embodiments of FIGS. 9-20. Please observe that the switch simply could mean any electronic circuit or component.

The embodiments described in connection with FIGS. 20 and 21 identify a method and a system for controlling transmission of wireless energy to implanted energy consuming components of an electrically operable apparatus. Such a method and system will be defined in general terms in the following.

A method is thus provided for controlling transmission of wireless energy supplied to implanted energy consuming components of an apparatus as described above. The wireless energy E is transmitted from an external energy source located outside the patient and is received by an internal energy receiver located inside the patient, the internal energy receiver being connected to the implanted energy consuming components of the apparatus for directly or indirectly supplying received energy thereto. An energy balance is determined between the energy received by the internal energy receiver and the energy used for the apparatus. The transmission of wireless energy E from the external energy source is then controlled based on the determined energy balance.

The wireless energy may be transmitted inductively from a primary coil in the external energy source to a secondary coil in the internal energy receiver. A change in the energy balance may be detected to control the transmission of wireless energy based on the detected energy balance change. A difference may also be detected between energy received by the internal energy receiver and energy used for the medical device, to control the transmission of wireless energy based on the detected energy difference.

When controlling the energy transmission, the amount of transmitted wireless energy may be decreased if the detected energy balance change implies that the energy balance is increasing, or vice versa. The decrease/increase of energy transmission may further correspond to a detected change rate.

The amount of transmitted wireless energy may further be decreased if the detected energy difference implies that the received energy is greater than the used energy, or vice versa. The decrease/increase of energy transmission may then correspond to the magnitude of the detected energy difference.

As mentioned above, the energy used for the medical device may be consumed to operate the medical device, and/or stored in at least one energy storage device of the medical device.

When electrical and/or physical parameters of the medical device and/or physical parameters of the patient are determined, the energy may be transmitted for consumption and storage according to a transmission rate per time unit which is determined based on said parameters. The total amount of transmitted energy may also be determined based on said parameters.

When a difference is detected between the total amount of energy received by the internal energy receiver and the total amount of consumed and/or stored energy, and the detected difference is related to the integral over time of at least one measured electrical parameter related to said energy balance, the integral may be determined for a monitored voltage and/or current related to the energy balance.

When the derivative is determined over time of a measured electrical parameter related to the amount of consumed and/or stored energy, the derivative may be determined for a monitored voltage and/or current related to the energy balance.

The transmission of wireless energy from the external energy source may be controlled by applying to the external energy source electrical pulses from a first electric circuit to transmit the wireless energy, the electrical pulses having leading and trailing edges, varying the lengths of first time intervals between successive leading and trailing edges of the electrical pulses and/or the lengths of second time intervals between successive trailing and leading edges of the electrical pulses, and transmitting wireless energy, the transmitted energy generated from the electrical pulses having a varied power, the varying of the power depending on the lengths of the first and/or second time intervals.

In that case, the frequency of the electrical pulses may be substantially constant when varying the first and/or second time intervals. When applying electrical pulses, the electrical pulses may remain unchanged, except for varying the first and/or second time intervals. The amplitude of the electrical pulses may be substantially constant when varying the first and/or second time intervals. Further, the electrical pulses may be varied by only varying the lengths of first time intervals between successive leading and trailing edges of the electrical pulses.

A train of two or more electrical pulses may be supplied in a row, wherein when applying the train of pulses, the train having a first electrical pulse at the start of the pulse train and having a second electrical pulse at the end of the pulse train, two or more pulse trains may be supplied in a row, wherein the lengths of the second time intervals between successive trailing edge of the second electrical pulse in a first pulse train and leading edge of the first electrical pulse of a second pulse train are varied.

When applying the electrical pulses, the electrical pulses may have a substantially constant current and a substantially constant voltage. The electrical pulses may also have a substantially constant current and a substantially constant voltage. Further, the electrical pulses may also have a substantially constant frequency. The electrical pulses within a pulse train may likewise have a substantially constant frequency.

The circuit formed by the first electric circuit and the external energy source may have a first characteristic time period or first time constant, and when effectively varying the transmitted energy, such frequency time period may be in the range of the first characteristic time period or time constant or shorter.

A system comprising an apparatus as described above is thus also provided for controlling transmission of wireless energy supplied to implanted energy consuming components of the apparatus. In its broadest sense, the system comprises a control device for controlling the transmission of wireless energy from an energy-transmission device, and an implantable internal energy receiver for receiving the transmitted wireless energy, the internal energy receiver being connected to implantable energy consuming components of the apparatus for directly or indirectly supplying received energy thereto.

The system further comprises a determination device adapted to determine an energy balance between the energy received by the internal energy receiver and the energy used for the implantable energy consuming components of the apparatus, wherein the control device controls the transmission of wireless energy from the external energy-transmission device, based on the energy balance determined by the determination device.

Further, the system may comprise any of the following:
- A primary coil in the external energy source adapted to transmit the wireless energy inductively to a secondary coil in the internal energy receiver.
- The determination device is adapted to detect a change in the energy balance, and the control device controls the transmission of wireless energy based on the detected energy balance change
- The determination device is adapted to detect a difference between energy received by the internal energy receiver and energy used for the implantable energy consuming components of the apparatus, and the control device controls the transmission of wireless energy based on the detected energy difference.
- The control device controls the external energy-transmission device to decrease the amount of transmitted wireless energy if the detected energy balance change implies that the energy balance is increasing, or vice versa, wherein the decrease/increase of energy transmission corresponds to a detected change rate.

The control device controls the external energy-transmission device to decrease the amount of transmitted wireless energy if the detected energy difference implies that the received energy is greater than the used energy, or vice versa, wherein the decrease/increase of energy transmission corresponds to the magnitude of said detected energy difference.

The energy used for the apparatus is consumed to operate the apparatus, and/or stored in at least one energy storage device of the apparatus.

Where electrical and/or physical parameters of the apparatus and/or physical parameters of the patient are determined, the energy-transmission device transmits the energy for consumption and storage according to a transmission rate per time unit which is determined by the determination device based on said parameters. The determination device also determines the total amount of transmitted energy based on said parameters.

When a difference is detected between the total amount of energy received by the internal energy receiver and the total amount of consumed and/or stored energy, and the detected difference is related to the integral over time of at least one measured electrical parameter related to the energy balance, the determination device determines the integral for a monitored voltage and/or current related to the energy balance.

When the derivative is determined over time of a measured electrical parameter related to the amount of consumed and/or stored energy, the determination device determines the derivative for a monitored voltage and/or current related to the energy balance.

The energy-transmission device comprises a coil placed externally to the human body, and an electric circuit is provided to power the external coil with electrical pulses to transmit the wireless energy. The electrical pulses have leading and trailing edges, and the electric circuit is adapted to vary first time intervals between successive leading and trailing edges and/or second time intervals between successive trailing and leading edges of the electrical pulses to vary the power of the transmitted wireless energy. As a result, the energy receiver receiving the transmitted wireless energy has a varied power.

The electric circuit is adapted to deliver the electrical pulses to remain unchanged except varying the first and/or second time intervals.

The electric circuit has a time constant and is adapted to vary the first and second time intervals only in the range of the first time constant, so that when the lengths of the first and/or second time intervals are varied, the transmitted power over the coil is varied.

The electric circuit is adapted to deliver the electrical pulses to be varied by only varying the lengths of first time intervals between successive leading and trailing edges of the electrical pulses.

The electric circuit is adapted to supplying a train of two or more electrical pulses in a row, said train having a first electrical pulse at the start of the pulse train and having a second electrical pulse at the end of the pulse train, and the lengths of the second time intervals between successive trailing edge of the second electrical pulse in a first pulse train and leading edge of the first electrical pulse of a second pulse train are varied by the first electronic circuit.

The electric circuit is adapted to provide the electrical pulses as pulses having a substantially constant height and/or amplitude and/or intensity and/or voltage and/or current and/or frequency.

The electric circuit has a time constant, and is adapted to vary the first and second time intervals only in the range of the first time constant, so that when the lengths of the first and/or second time intervals are varied, the transmitted power over the first coil are varied.

The electric circuit is adapted to provide the electrical pulses varying the lengths of the first and/or the second time intervals only within a range that includes the first time constant or that is located relatively close to the first time constant, compared to the magnitude of the first time constant.

While specific embodiments of the invention have been illustrated and described herein, it should be realized that numerous other embodiments may be envisaged and that numerous additional advantages, modifications and changes will readily occur to those skilled in the art without departing from the spirit and scope of the invention. Therefore, the invention in its broader aspects is not limited to the specific details, representative devices and illustrated examples shown and described herein. Accordingly, various modifications may be made without departing from the spirit or scope of the general inventive concept as defined by the appended claims and their equivalents, and numerous other embodiments may be envisaged without departing from the spirit and scope of the invention.

The invention claimed is:

1. A method for controlling a medical implant system in a mammal body, the system comprising a first and a second part being adapted for communication with each other, in which system the first part is adapted for implantation in the mammal body for the control of and communication with the medical implant, the second part is adapted to be worn on an outside of the mammal body in physical contact with said body and adapted to receive control voice commands from a user and to transmit these commands to the first part, the method comprising the steps of:
    using the mammal body as a conductor for the communication between the first and the second parts,
    receiving and recognizing by the second part the control commands from a user as voice commands,
    transforming recognized voice commands into signals which are transmitted to the first part via the mammal body as a conductor for the control of said implant,
    conveying such signals to the implant by the first part, and
    translating voice commands comprising a complex of different frequencies into one fixed defined output command by the second part,
    wherein the system comprises a first conducting plate in the first part of the system and a second conducting plate in the second part of the system, and the method further comprises the step of creating an electrical capacitive field with potential differences between said first and second conducting plates using the mammal body as the conductor.

2. The method of claim 1, comprising a detector circuit at least in the first part of the system, the method comprising the steps of:
    detecting potential differences between the conducting plates, and
    using the potential differences for said communication between the first and the second parts of the system.

3. The method according to claim 1, comprising a first and second conducting plate in each of the first and second parts of the system, the method further comprising the steps of:
creating an electrical field with potential differences between the first and second conducting plates in the second part of the system, the system further comprising a detector circuit in the first part of the system,
detecting variations in the potential difference in the first and second conducting plates, thereby communicating between the first and the second parts, and
using the potential differences for the communication between the first and the second parts of the system.

4. The method according to claim 3, in which at least one of the first and second conducting plates in each of the first and second parts of the system is covered by a dielectric material.

5. The method according to claim 1, wherein each of the first and second parts comprises a comparator for comparing at least two different received frequencies, the method further comprising the step of
comparing at least two different received frequencies as part of the communication between the first and second parts.

6. The method according to claim 1, in which said system comprises an ornament such as a necklace, a bracelet, a ring, an ear ring or a piercing ornament for the human body.

7. The method according to claim 1, in which said system comprises a watch or a wrist watch.

8. The method according to claim 2, wherein the steps of detecting the potential differences between the conducting plates, and using the potential differences for said communication between the first and the second parts of the system, further comprises the steps of:
creating the capacitive electrical field with potential differences between said plates, so that the communication between the first and second parts can be in either direction,
allowing both of the first and second parts to be either a sending part or a receiving part, in which system the second part comprises a detector circuit for detecting said potential difference, wherein the method further comprises the steps of:
interpreting the detected potential differences as said communication, and
presenting to the user, by the second part, received communications from the first part.

9. The method according to claim 8, the method further comprising the steps of:
creating and sending at least two different signal frequencies in the electrical field by the sending part,
receiving and detecting which frequency is being received from the electrical field, using a detector circuit in the receiving part, and
interpreting these at least two frequencies as the communication between the two parts.

10. The method according to claim 8, the method comprising the further steps of:
creating pulses with positive and negative amplitudes in the electrical field in the sending part, and
detecting said pulses with positive and negative amplitudes, and
interpreting these amplitudes as the communication between the two parts by the detector circuit of the receiving part.

11. The method according to claim 1, the method comprising the further step of reducing the electrical current which flows in the mammal body by using a high electrical resistance between the first and second parts of the system.

12. The method according to claim 11, wherein the electrical resistance is at least 1 Mega Ohm.

13. The method according to claim 1, in which at least one of the first part and the second part comprises a communication transceiver comprising at least a part of a capacitive energy storage, the method further comprising the step of
injecting or drawing an electrical current into or from the capacitive energy storage using the capacitive field for the communication.

14. The method according to claim 13, in which the second part comprises the communication transceiver, the second part further comprises a second part of a capacitive energy storage, the method further comprising the step of:
injecting or drawing an electrical current into or from a capacitive energy storage using the capacitive field for the communication.

15. The method according to claim 1, in which the communication between the first and second parts is performed digitally, the method further comprising the step of representing the information by variations of the derivative of the voltage over the capacitive energy storage.

16. The method according to claim 13, in which each of the first and second parts of the capacitive energy storage is divided into two separate portions, the method further comprising the steps of:
injecting or drawing an electrical current into or from one of the two separate portions, simultaneously, and
injecting or drawing an electrical current into or from, respectively, the other of the two separate portions.

17. The method according to claim 1, the system comprising at least one switch implantable in the patient for manually and non-invasively controlling the system, and
a wireless remote control for non-invasively controlling the system, the method further comprising the step of non-invasively controlling the apparatus by at least one of the wireless remote control and the implantable switch.

18. The method according to claim 1, the system comprising at least one of:
an internal energy source for powering implantable energy consuming components of the system, and
an internal energy receiver, adapted to be energized non-invasively and wirelessly by an energy transmission device from outside the patient's body,
the method further comprising the steps of sending wireless energy to at least one of:
the implantable internal energy source when comprised in the system, being chargeable by energy transferred from an energy transmission device, and
the internal energy receiver when comprised in the system, supplying energy to at least one implantable energy consuming component of the system, being energised by the wireless energy.

19. The method according to claim 1, wherein the system comprises a sensor and/or a measuring device, the method further comprising the steps of
sensing or measuring at least one of:
at least one physical parameter of the patient, and
at least one functional parameter related to the system, the functional parameter comprising at least one of:
a functional parameter correlated to the transfer of energy for charging an internal energy source, and
a functional parameter related to the system,
sending feedback information using a feedback device from inside the patient's body to at least one of:

an implantable internal control unit comprised, and
an external control unit outside of the patients body, via the internal control unit, wherein the internal control unit being adapted to be programmed to regulate the system according to a pre-programmed time-schedule or to input from any sensor sensing any possible physical parameter of the patient or any functional parameter of the system, and wherein the feedback information being related to at least one of:

the at least one physical parameter of the patient, and the at least one functional parameter related to the system.

20. The method according to claim 1, wherein said second part comprises a learning device adapted to successively learn the voice commands and learn to combine with the right output command, the method further comprising the steps of:

learning the voice commands and learning to combine with the right output command, recognizing by the learning device to approximate voice commands into a fixed defined output command, wherein said voice commands comprise a complex of different frequencies, translating the voice commands into one fixed defined output command, and summarizing a defined input of different frequencies into one single action, wherein said output commands do not differentiate different frequencies.

* * * * *